United States Patent
Li et al.

(10) Patent No.: US 12,122,792 B2
(45) Date of Patent: *Oct. 22, 2024

(54) PHARMACEUTICAL COMPOSITIONS COMPRISING 4-((6bR,10aS)-3-METHYL2,3,6b,9,10,10a-HEXAHYDRO-1H-PYRIDO[3',4':4,5]PYRROLO[1,2,3-de]QUINOXALIN8(7H)-yl)-1-(4-((6bR,10aS)-3-METHYL-2,3,6b,9,10,10a-HEXAHYDRO-1H-PYRIDO[3',4':4,5]PYRROLO[1,2,3-de]QUINOXALIN-8(7H)-yl)PHENYL)BUTAN-1-ONE FOR TREATING CONDITIONS OF THE CENTRAL NERVOUS SYSTEM AND CARDIAC DISORDERS

(71) Applicant: INTRA-CELLULAR THERAPIES, INC., New York, NY (US)

(72) Inventors: Peng Li, New Milford, NJ (US); Robert E Davis, San Diego, CA (US); Kimberly Vanover, New York, NY (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/240,951

(22) Filed: Aug. 31, 2023

(65) Prior Publication Data
US 2024/0002403 A1 Jan. 4, 2024

Related U.S. Application Data

(63) Continuation of application No. 17/757,212, filed as application No. PCT/US2020/064338 on Dec. 10, 2020, now Pat. No. 11,753,419.

(60) Provisional application No. 62/946,568, filed on Dec. 11, 2019.

(51) Int. Cl.
| | |
|---|---|
| *A61K 31/4985* | (2006.01) |
| *C07D 471/22* | (2006.01) |
| *C07D 487/22* | (2006.01) |
| *C07D 519/00* | (2006.01) |

(52) U.S. Cl.
CPC .................. *C07D 519/00* (2013.01)

(58) Field of Classification Search
CPC . A61K 31/4985; C07D 471/22; C07D 487/22
USPC ............... 514/250; 544/343; 546/64
See application file for complete search history.

(56) References Cited

U.S. PATENT DOCUMENTS

| | | |
|---|---|---|
| 3,299,078 A | 1/1967 | Pachter |
| 3,813,392 A | 5/1974 | Sellstedt et al. |
| 4,001,263 A | 1/1977 | Plattner et al. |
| 4,238,607 A | 12/1980 | Rajagopalan |
| 4,389,330 A | 6/1983 | Tice et al. |
| 4,530,840 A | 7/1985 | Tice et al. |
| 4,767,628 A | 8/1988 | Hutchinson |
| 5,004,602 A | 4/1991 | Hutchinson |
| 5,114,976 A | 5/1992 | Norden |
| 5,151,419 A | 9/1992 | Perenyi et al. |
| 5,538,739 A | 7/1996 | Bodmer et al. |
| 6,407,092 B1 | 6/2002 | Hester et al. |
| 6,544,599 B1 | 4/2003 | Mesens et al. |
| 6,548,493 B1 | 4/2003 | Robichaud et al. |
| 6,552,017 B1 | 4/2003 | Robichaud et al. |
| 6,699,852 B2 | 3/2004 | Robichaud et al. |
| 6,713,471 B1 | 3/2004 | Robichaud et al. |
| 6,849,619 B2 | 2/2005 | Robichaud et al. |
| 6,849,640 B2 | 2/2005 | Ennis et al. |
| 7,071,186 B2 | 7/2006 | Robichaud et al. |
| 7,081,455 B2 | 7/2006 | Robichaud et al. |

(Continued)

FOREIGN PATENT DOCUMENTS

| | | |
|---|---|---|
| EP | 1 564 671 | 8/2005 |
| WO | WO 2000/064899 | 11/2000 |

(Continued)

OTHER PUBLICATIONS

U.S. Appl. No. 14/627,968, filed Feb. 20, 2015, Mates, et al.

(Continued)

*Primary Examiner* — Douglas M Willis
(74) *Attorney, Agent, or Firm* — Hoxie & Associates LLC

(57) ABSTRACT

The invention relates to pharmaceutical compositions comprising the compound of Formula I,

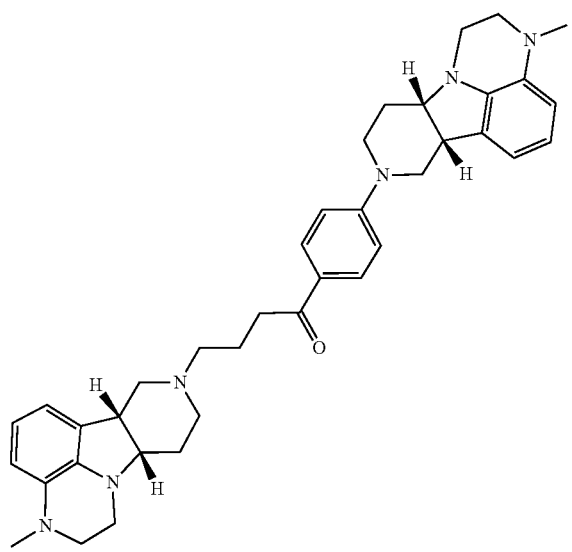

and new methods and uses pertaining thereto, and pharmaceutical compositions thereof, such as methods of use in the treatment of diseases involving the 5-HT receptor, the serotonin transporter (SERT), and/or pathways involving dopamine $D_2$ receptor signaling, sodium channel activity, and/or norepinephrine transporter activity.

35 Claims, No Drawings

(56) References Cited

U.S. PATENT DOCUMENTS

| | | |
|---|---|---|
| 7,109,339 B2 | 9/2006 | Lee et al. |
| 7,183,282 B2 | 2/2007 | Robichaud et al. |
| RE39,679 E | 6/2007 | Robichaud et al. |
| RE39,680 E | 6/2007 | Robichaud et al. |
| 7,238,690 B2 | 7/2007 | Robichaud et al. |
| 7,375,226 B2 | 5/2008 | Jolidon et al. |
| 7,592,454 B2 | 9/2009 | Lee et al. |
| 7,645,752 B2 | 1/2010 | McDevitt et al. |
| 8,309,722 B2 | 11/2012 | Tomesch et al. |
| 8,598,119 B2 | 12/2013 | Mates et al. |
| 8,648,077 B2 | 2/2014 | Tomesch et al. |
| 8,779,139 B2 | 7/2014 | Tomesch et al. |
| 8,993,572 B2 | 3/2015 | Mates et al. |
| 9,161,061 B2 | 10/2015 | Mesh-Iliescu et al. |
| 9,168,258 B2 | 10/2015 | Mates et al. |
| 9,199,995 B2 | 12/2015 | Tomesch et al. |
| 9,315,504 B2 | 4/2016 | Tomesch et al. |
| 9,371,324 B2 | 6/2016 | Mates et al. |
| 9,393,192 B2 | 7/2016 | Yam et al. |
| 9,428,506 B2 | 8/2016 | Mates et al. |
| 9,586,960 B2 | 3/2017 | Tomesch et al. |
| 9,616,061 B2 | 4/2017 | Mates et al. |
| 9,708,322 B2 | 7/2017 | Li et al. |
| 9,745,300 B2 | 8/2017 | Mates et al. |
| 9,751,883 B2 | 9/2017 | Tomesch et al. |
| 9,956,227 B2 | 5/2018 | Vanover et al. |
| 10,072,010 B2 | 9/2018 | Li et al. |
| 10,077,267 B2 | 9/2018 | Mates et al. |
| 10,117,867 B2 | 11/2018 | Mates et al. |
| 10,221,176 B2 | 3/2019 | Tomesch et al. |
| 10,245,260 B2 | 4/2019 | Yao et al. |
| 10,322,134 B2 | 7/2019 | Vanover et al. |
| 10,464,938 B2 | 11/2019 | Tomesch et al. |
| 10,472,359 B2 | 11/2019 | Li et al. |
| 10,597,394 B2 | 3/2020 | Mates et al. |
| 10,654,854 B2 | 5/2020 | Li et al. |
| 10,688,097 B2 | 6/2020 | Yao et al. |
| 10,702,522 B2 | 7/2020 | Mates et al. |
| 10,716,786 B2 | 7/2020 | Li et al. |
| 10,799,500 B2 | 10/2020 | Yao et al. |
| 10,844,061 B2 | 11/2020 | Li et al. |
| 10,899,762 B2 | 1/2021 | Mates et al. |
| 10,906,906 B2 | 2/2021 | Li et al. |
| 10,960,009 B2 | 3/2021 | Vanover et al. |
| 10,960,010 B2 | 3/2021 | Vanover et al. |
| 10,961,245 B2 | 3/2021 | Li et al. |
| 11,014,925 B2 | 5/2021 | Li et al. |
| 11,026,951 B2 | 6/2021 | Mates et al. |
| 11,052,083 B2 | 7/2021 | Li et al. |
| 11,053,245 B2 | 7/2021 | Mates et al. |
| 11,066,407 B2 | 7/2021 | Tomesch et al. |
| 11,096,944 B2 | 8/2021 | Yao et al. |
| 11,124,514 B2 | 9/2021 | Mates et al. |
| RE48,839 E | 12/2021 | Mates et al. |
| 11,311,536 B2 | 4/2022 | Li et al. |
| 11,331,316 B2 | 5/2022 | Li et al. |
| 11,376,249 B2 | 7/2022 | Li et al. |
| 11,407,751 B2 | 8/2022 | Tomesch et al. |
| 11,427,587 B2 | 8/2022 | Li et al. |
| 11,453,670 B2 | 9/2022 | Li et al. |
| 11,560,382 B2 | 1/2023 | Mates et al. |
| 11,680,065 B2 | 6/2023 | Li et al. |
| 11,723,909 B2 | 8/2023 | Yao et al. |
| 11,806,347 B2 | 11/2023 | Li et al. |
| 2004/0220178 A1 | 11/2004 | Robichaud et al. |
| 2011/0269777 A1 | 11/2011 | Bachurin et al. |
| 2019/0211015 A1 | 7/2019 | Mittelman et al. |
| 2019/0388418 A1 | 12/2019 | Li et al. |
| 2020/0087305 A1 | 3/2020 | Tomesch et al. |
| 2020/0102304 A1 | 4/2020 | Li et al. |
| 2020/0102309 A1 | 4/2020 | Li et al. |
| 2020/0157100 A1 | 5/2020 | Li |
| 2020/0392135 A1 | 12/2020 | Wennogle et al. |
| 2020/0405713 A1 | 12/2020 | Mates et al. |
| 2020/0407362 A1 | 12/2020 | Mates et al. |
| 2021/0002280 A1 | 1/2021 | Mates et al. |
| 2021/0008065 A1 | 1/2021 | Li et al. |
| 2021/0009592 A1 | 1/2021 | Li et al. |
| 2021/0060009 A1 | 3/2021 | Snyder et al. |
| 2021/0070755 A1 | 3/2021 | Berecz et al. |
| 2021/0315891 A1 | 10/2021 | Li et al. |
| 2022/0362241 A1 | 11/2022 | Davis et al. |
| 2023/0372336 A1 | 11/2023 | Dutheil et al. |

FOREIGN PATENT DOCUMENTS

| | | |
|---|---|---|
| WO | WO 2003/091250 A1 | 11/2003 |
| WO | WO 2008/112280 A1 | 11/2008 |
| WO | WO 2017/117514 | 7/2017 |
| WO | WO 2018/031535 | 2/2018 |
| WO | WO 2018/106916 | 6/2018 |
| WO | WO 2019/102240 A1 | 5/2019 |
| WO | WO 2021/119334 | 6/2021 |

OTHER PUBLICATIONS

Aiken, C., "An Overview of Atypical Antipsychotics for Bipolar Depression," published on Jan. 3, 2020 at https://www.psychiatrictimes.com/view/overview-atypical-antipsychotics-bipolar-depression, 11 pages.

Barman et al., "Newer Antipsychotics: Brexpiprazole, Cariprazine, and Lumateperone: A Pledge or Another Unkept Promise?," World J. Psychiatr., vol. 11, No. 12, p. 1228-1238, (2021).

Barry et al., "Schizophrenia," *Clinical Evidence*, 06(1007): 1-170 (2012).

Bastin, "Salt Selection and Optimized Procedures for Pharmaceutical New Chemical Entities", Organic Process and Research Development, vol. 4, No. 5, pp. 427-435 (2000).

Bryan-Lluka, L. J. et al., "Potencies of haloperidol metabolites as inhibitors of the human noradrenaline, dopamine and serotonin transporters in transfected COS-7 cells", Naunyn-Shemiedeberg's Arch Pharmacol, 1999, vol. 360, pp. 109-115.

Calabrese et al., "Efficacy and Safety of Lumateperone for Major Depressive Episodes Associated with Bipolar I or Bipolar II Disorder: A Phase 3 Randomized Placebo-Controlled Trial," American Journal of Psychiatry, vol. 178, No. 12, p. 1098-1106, (2021), published online Sep. 23, 2021, <<https://doi.org/10.1176/appi.aip.2021.20091339>>.

"Clinical Trial Evaluating ITI-007 (Lumateperone) as a Monotherapy for the Treatment of Bipolar," ClinicalTrials.gov (Identifier: NCT02600494), 5 pages, (2015).

Correll et al., "Efficacy and Safety of Lumateperone for Treatment of Schizophrenia: A Randomized Clinical Trial," JAMA Psychiatry, vol. 77, No. 4, p. 349-358 (2020).

Darmani, N. A., et al., "Do Functional Relationships Exist Between 5-HT$_{1A}$ and 5-HT$_2$ Receptors?," *Pharmacology and Biochemistry & Behavior*, vol. 36, p. 901-906, (1990).

Davis, et al., "ITI-007 in the treatment of schizophrenia: from novel pharmacology to clinical outcomes," Expert Review of Neurotherapeutics, vol. 16, No. 6, pp. 601-614, (2016).

Davis et al. "ITI-007 demonstrates brain occupancy at serotonin 5-HT2A and dopamine D2 receptors and serotonin transporters using positron emission tomography in healthy volunteers", Psychopharmacology, Published Online Apr. 7, 2015, pp. 1-10.

Davis, et al., "Lumateperone (ITI-007), A Novel Drug in Development for the Treatment of Agitation in Patients with Dementia, including Alzheimer's Disease: Rationale and Clinical Design," The Journal of Prevention of Alzheimer's Disease, 4(4):372 (2017) (Clinical Trials in Alzheimer's Disease (CTAD) Congress, Symposium Summary P93).

Davis et al., "Rationale for the Development of Low Doses of ITI-007 for the Treatment of Behavioral Disturbances Associated with Dementia," The Journal of Prevention of Alzheimer's Disease, 2(4):302 (2015) (Clinical Trials in Alzheimer's Disease (CTAD) Congress, Symposium Summary OC51).

Davis et al., "ITI-007: A Novel Treatment for Behavioral Disturbances Associated with Dementia and Related Disorders," Clinical Trials in Alzheimer's Disease (CTAD) Congress 2014 (2014) (poster presentation).

(56) References Cited

OTHER PUBLICATIONS

Edinoff et al., "Lumateperone for the Treatment of Schizophrenia," Psychopharmacology Bulletin, vol. 50, No. 4, p. 32-59 (2020).

Gramigna, J, "Lumateperone Safe, Effective for Depressive Symptoms Among Patients with Bipolar Disorders," American Society of Clinical Psychopharmacology Annual Meeting, Jun. 2, 2020, 3 pages.

Hackam, et al., "Translation of Research Evidence from Animals to Humans," JAMA, vol. 296, No. 14, pp. 1731-1732, (2006).

Harvey, et al., "Lumateperone Improves Negative Symptoms Related to Emotional Experience (Avolition) in Patient with Schizophrenia," Abstract presented at the American Society of Clinical Psychopharmacology (ASCP) Annual Meeting; May 29-Jun. 1, 2018; Miami, FL.

Hlavinka, E., "Schizophrenia Tx Eases Depression in Bipolar Disorder: Lumateperone Offers Greater Rate of Response, Remission versus Placebo," Medpage Today, 7 pages, (2020); https://www.medpagetoday.com/meetingcoverage/psychcongress/88584.

ITI-007 in the treatment of schizophrenia: from novel pharmacology to clinical outcomes. Expert Review of Neurotherapeutics, vol. 16, No. 6, pp. 601-614, (2016).

Jordan, V. C. Nature Reviews: Drug Discovery, 2, 2003, pp. 205-213.

Kahn, et al., "Residual Symptoms of Schiziphrenia. What are Realistic Treatment Goals? Lingering Symptoms Require you to Evaluate Pharmacotherapy and Offer Psychosocial Interventions," *Current Psychiatry*, vol. 16, No. 3, pp. 35-40, (2017).

Kay, S.R., et al., "The Positive and Negative Syndrome Scale (PANSS) for Schizophrenia," *Schizophrenia Bulletin*, vol. 13, Issue 2, pp. 261-276, (1987).

Kendrick, "The Newer, 'Atypical' Antipsychotic Drugs—Their Development and Current Therapeutic Use," British J. General Practice, vol. 49, p. 745-749 (1999).

Khorana, et al., "Gamma-Carbolines: Binding at 5-HT5A Serotonin Receptors", Bioorganic & Medicinal Chemistry, (2003), vol. 11, Issue 5, 6, pp. 717-722, p. 718 Table 1.

Kumar et al., "Lumateperone: A New Treatment Approach for Neuropsychiatric Disorders," Drugs of Today, vol. 54, No. 12, p. 713-719, (2018).

Lammers, et al., "Risperidone Long-acting Injection in Schizophrenia Spectrum Illnesses Compared to First Generation Depot Antipsychotics in an Outpatient Setting in Canada," BMC Psychiatry, vol. 13, No. 155, 9 pages, (2013); http://www.biomedcentral.com/1471-244X/13/155.

Lee et al. "Novel, Highly Potent, Selective 5-HT2A/D2 Receptor Antagonists as Potential Atypical Antipsychotics," Bioorg. Med. Chem. Lett. vol. 13, p. 767-770, (2003).

Li et al., "Discovery of a Tetracyclic Quinoxaline Derivative as a Potent and Orally Active Multifunctional Drug Candidate for the Treatment of Neuropsychiatric and Neurological Disorders", vol. 57, pp. 2670-2682 (2014).

Lieberman, J.A., et al., "ITI-007 for the Treatment of Schizophrenia: A 4-Week Randomized, Double-Blind, Controlled Trial," *Biol. Psychiatry*, 79(12), pp. 952-961, (2015).

Makadia et al., "Poly Lactic-co-Glycolic Acid (PLGA) as Biodegradable Controlled Drug Delivery Carrier," Polymers (Basel), vol. 3, No. 3, pp. 1377-1397, (2011).

Marek et al. Synergistic Action of 5-HT2A Antagonists and Selective Serotonin Reuptake Inhibitors in Neuropsychiatric Disorders. Neuropsychopharmacology, 2003. vol. 28, pp. 402-412. (Year: 2003).

Mcintyre et al., "Rapid-acting Antidepressants in Psychiatry: Psychedelics, Episodic Treatments, Innovation, and Clarion Call for Methodologic Rigor in Drug Development," Expert Opinion on Drug Safety, vol. 21, No. 6, p. 715-716, (2022).

O'Gorman, et al., "Lumateperone (ITI-007): A Novel Investigational Agent with Broad Therapeutic Potential Across Multiple Neuropsychiatric Disorders," Poster P.1.g.038, European College of Neuropsychopharmacology (ECNP) Congress (2017).

Press Release, "Intra-Cellular Therapies Announces Additional Results From Phase I/II Clinical Trial for ITI-007 in Healthy Geriatric Subjects and Patients With Dementia.", Intra-Cellular Therapies, Press Release Date: Nov. 21, 2014, (http://ir.intracellulartherapies.com/releasedetail.cfm?ReleaseID=884325), accessed on May 31, 2016.

Press Release, "Intra-Cellular Therapies Presents Data on Symptom Improvement by Lumateperone on Negative Symptoms, Depression, and Social Function in Patients with Schizophrenia at the American Society of Clinical Psychopharmacology (ASCP) Annual Meeting," Intra-Cellular Therapies, Press Release Date: May 31, 2018, (https://ir.intracellulartherapies.com/newsreleases/.

Press Release, "Intra-Cellular Therapies Announces Positive Top-Line Results from a Phase 3 Trial of Lumateperone in Patient with Bipolar Depression," Intra-Cellular Therapies, Press Release Date: Jul. 8, 2019.

PubChem, OPEN Chemistry Database, Compound Summary for CID-22036753, pp. 4, (2007), 12 pages.

Pubchem, CID-9953107, p. 3, pp. 1-9 (2006).

PubChem, OPEN Chemistry Database, PubChem SID 103920954, PubChem CID 90655118, (2011), 6 pages.

Rainer, M.K., "Risperidone Long-acting Injection: A Review of its Long Term Safety and Efficacy," *Neuropsychiatric Disease and Treatment*, vol. 4, No. 5, pp. 919-927, (2008).

Satlin, et al., "ITI-007 (Lumateperone) for the Treatment of Agitation in Patients with Dementia, including Alzheimer's Disease," Alzheimer's & Dementia 14(7) (Suppl.): P678-79 (2018) (Alzheimer's Assoc. International Conference 2018, summary of Poster P2-032).

Satlin, et al., "ITI-007 (Lumateperone) for the Treatment of Agitation in Patients with Dementia, including Alzheimer's Disease," Poster P2-032, Alzheimer's Assoc. International Conference 2018 (2018).

Snyder et al., "Functional profile of a novel modulator of serotonin, dopamine, and glutamate neurotransmission", *Psychopharmacology*, 232:605-621 (2015).

Tohen, M., et al., "Efficacy of Olanzapine and Olanzapine-Fluoxetine Combination in the Treatment of Bipolar I Depression," Arch Gen Psychiatry, vol. 60, pp. 1079-1088, (2003).

Vanover, et al., "Dopamine D2 receptor occupancy of lumateperone (ITI-007): a Positron Emission Tomography Study in patients with schizophrenia," Neuropsychopharmacology 44:598-605, (2019).

Vanover, et al., "A Novel Approach to Address an Unmet Need in the Treatment of Schizophrenia and Depression: Lumateperone, an Innovative Modulator of Dopamine, Serotonin, and Glutamate," Abstract presented at the American Society of Clinical Psychopharmacology (ASCP) Annual Meeting; May 29-Jun. 1, 2018; Miami, FL.

Vanover, et al., "Lumateperone (ITI-007): A Novel Investigational Agent with Broad Therapeutic Potential Across Multiple Neuropsychiatric Disorders," *European Neuropsychopharmacology*, 27:S660-61 (2017) (Summary of ECNP Poster P.1.g.038).

Vyas, P., et al., "An Evaluation of Lumateperone Tosylate for the Treatment of Schizophrenia," *Expert Opinion on Pharmacotherapy*, vol. 21, No. 2, pp. 139-145, (2020); https://doi.org/10.1080/14656566.2019.1695778.

Wang et al., "Rapid-acting Antidepressants Targeting Modulation of the Glutamatergic System: Clinical and Preclinical Evidence and Mechanisms," General Psychiatry, vol. 35, No. e100922, 6 pages (2022).

Witkin et al., "Chapter 3: Rapid-acting Antidepressants," Advances in Pharmacology, vol. 86, 50 pages, 2019.

Intra-Cellular Therapies, Inc., "Corporate Presentation" (Sep. 24, 2019), downloaded from https://ir.intracellulartherapies.com/static-files/93b08960-f01c-4864-aa22-8cadb3539753 (last accessed Mar. 13, 2023).

"Clinical Trial Evaluating ITI-007 as an Adjunctive Therapy to Lithium or Valproate for the Treatment of Bipolar Depression," ClinicalTrials.gov, 6 pages, Nov. 9, 2015.

"Study of a Novel Antipsychotic ITI-007 in Schizophrenia," Clinical Trials.gov, 6 pages, Dec. 26, 2011.

Calabrese et al., "Efficacy and Safety of Lumateperone for Major Depressive Episodes Associated with Bipolar I or Bipolar II Dis-

(56) References Cited

OTHER PUBLICATIONS order: A Phase 3 Randomized Placebo-Controlled Trial," Am J Psychiatry, vol. 178, No. 12, p. 1098-1106, (2021).
Kantrowitz, J.T., "The Potential Role of Lumateperone-Something Borrowed? Something New?," JAMA Psychiatry, vol. 77, No. 4, p. 343-344, (2020); Abstract Only.
Mcintyre et al., "The Efficacy of Lumateperone in Patients with Bipolar Depression with Mixed Features," J Clin Psychiatry, vol. 84, No. 3, 10 pages, (2023).
Mcintyre et al., "The Efficacy of Lumateperone on Symptoms of Depression in Bipolar I and Bipolar II Disorder: Secondary and Post Hoc Analyses," European Neuropsychopharmacology, vol. 68, p. 78-88, (2023).
Newton, W., "Intra Intra-Cellular reports positive Phase III trial of Caplyta in MDD and bipolar depression," ClinicalTrials Arena, Mar. 29, 2023, retrieved from https://www.clinicaltrialsarena.com/news/news-intra-cellular-positive-phase-iii-trial/ (last accessed, Mar. 7, 2024).
Vanover et al., Abstracts of the $13^{th}$ International Congress on Schizophrenia (ICOSR) (Apr. 2-6, 2011), Schizophrenia Bull. 37 Suppl. 1., p. 325 (Mar. 2011).
Wennogle, et al., "Activation of NMDA and AMPA Receptors by Lumateperone (ITI-007): Implications for Antidepressant Activity," Abstract presented at the 2017 Collegium Internationale Neuro-Psychopharmacologicum (CINP) Thematic Meeting: Treatment Resistant Depression; Jul. 20-22, 2017; Prague.

PHARMACEUTICAL COMPOSITIONS COMPRISING 4-((6bR,10aS)-3-METHYL2,3,6b,9,10,10a-HEXAHYDRO-1H-PYRIDO[3',4':4,5] PYRROLO[1,2,3-de]QUINOXALIN8(7H)-yl)-1-(4-((6bR,10aS)-3-METHYL-2,3,6b,9,10,10a-HEXAHYDRO-1H-PYRIDO[3',4':4,5] PYRROLO[1,2,3-de]QUINOXALIN-8(7H)-yl)PHENYL)BUTAN-1-ONE FOR TREATING CONDITIONS OF THE CENTRAL NERVOUS SYSTEM AND CARDIAC DISORDERS

CROSS REFERENCE TO RELATED APPLICATIONS

This application is an a continuation of U.S. application Ser. No. 17/757,212, filed on Jun. 10, 2022, which is a national stage application filed under 35 U.S.C. § 371 claiming priority to international application No. PCT/US2020/064338, filed on Dec. 10, 2020, which claims priority to and the benefit of U.S. Provisional Application Ser. No. 62/946,568, filed on Dec. 11, 2019, the contents of each of which are hereby incorporated by reference in their entireties.

FIELD OF THE INVENTION

The invention relates to a new compound, a particular substituted heterocycle fused gamma-carboline, and new methods and uses pertaining thereto, and pharmaceutical compositions thereof, such as methods of use in the treatment of diseases involving the 5-HT receptor, the serotonin transporter (SERT), and/or pathways involving dopamine $D_2$ receptor signaling, sodium channel activity, and/or norepinephrine transporter activity, e.g., diseases or disorders such as anxiety, psychosis, schizophrenia, sleep disorders, sexual disorders, migraine, conditions associated with cephalic pain, social phobias, gastrointestinal disorders such as dysfunction of the gastrointestinal tract motility and obesity; depression and mood disorders associated with psychosis or Parkinson's disease; psychosis such as schizophrenia associated with depression; bipolar disorder; mood disorders; and other psychiatric and neurological conditions, as well as to combinations with other agents.

BACKGROUND OF THE INVENTION

Substituted heterocycle fused gamma-carbolines are known to be agonists or antagonists of 5-$HT_2$ receptors, particularly 5-$HT_{2A}$ and 5-$HT_{2C}$ receptors, in treating central nervous system disorders. These compounds have been disclosed in U.S. Pat. Nos. 6,548,493; 7,238,690; 6,552,017; 6,713,471; 7,183,282; U.S. RE39680, and U.S. RE39679, as novel compounds useful for the treatment of disorders associated with 5-$HT_{2A}$ receptor modulation such as obesity, anxiety, depression, psychosis, schizophrenia, sleep disorders, sexual disorders migraine, conditions associated with cephalic pain, social phobias, gastrointestinal disorders such as dysfunction of the gastrointestinal tract motility, and obesity. Methods of making substituted heterocycle fused gamma-carbolines and uses of these gamma-carbolines as serotonin agonists and antagonists useful for the control and prevention of central nervous system disorders such as addictive behavior and sleep disorders are disclosed in U.S. Pat. Nos. 7,081,455; 7,071,186; 7,183,282; 8,309,722; 8,779,139; 9,315,504; 9,751,883; 10,221,176; and in applications PCT/US2019/36593 and Ser. No. 16/438,163, the contents of each of which are hereby incorporated by reference in their entireties.

In addition, U.S. Pat. No. 8,598,119 discloses use of particular substituted heterocycle fused gamma-carbolines for the treatment of a combination of psychosis and depressive disorders as well as sleep, depressive and/or mood disorders in patients with psychosis or Parkinson's disease. In addition to disorders associated with psychosis and/or depression, this patent application discloses and claims use of these compounds at a low dose to selectively antagonize 5-$HT_{2A}$ receptors without affecting or minimally affecting dopamine $D_2$ receptors, thereby useful for the treatment of sleep disorders without the side effects associated with high occupancy of the dopamine $D_2$ pathways or side effects of other pathways (e.g., $GABA_A$ receptors) associated with convention sedative-hypnotic agents (e.g., benzodiazepines) including but not limited to the development of drug dependency, muscle hypotonia, weakness, headache, blurred vision, vertigo, nausea, vomiting, epigastric distress, diarrhea, joint pains, and chest pains. U.S. Pat. No. 8,648,077 also discloses of methods of preparing toluenesulfonic acid addition salt crystals of these substituted heterocycle fused gamma-carbolines.

One particular fused heterocycle gamma carboline, 4-((6bR,10aS)-3-methyl-2,3,6b,9,10,10a-hexahydro-1H-pyrido[3',4': 4,5]pyrrolo[1,2,3-de]quinoxalin-8(7H)-yl)-1-(4-fluorophenyl)-1-butanone, is disclosed in, for example, US 2011/0071080, US 2015/0072964, US 2015/0080404, and US 2016/0310503. This compound is a potent serotonin 5-$HT_{2A}$ receptor antagonist, dopamine receptor D1 and D2 modulator, and scrotonin transporter (SERT) antagonist.

4-((6bR,10aS)-3-methyl-2,3,6b,9,10,10a-hexahydro-1H-pyrido[3',4': 4,5]pyrrolo[1,2,3-de]quinoxalin-8(7H)-yl)-1-(4-fluorophenyl)-1-butanone, also known as lumateperone, has also been approved for the treatment of schizophrenia in the United States (as CAPLYTA®), and it has completed Phase II and/or Phase III clinical trials for the treatment of agitation associated with dementia, and bipolar depression.

There remains a need for additional compounds having strong serotonin receptor, serotonin transporter (SERT), and/or dopamine $D_2$ receptor activities, and other biological activities.

SUMMARY OF THE INVENTION

The present disclosure relates to the Compound of Formula I, in free or pharmaceutically acceptable salt form, as shown below:

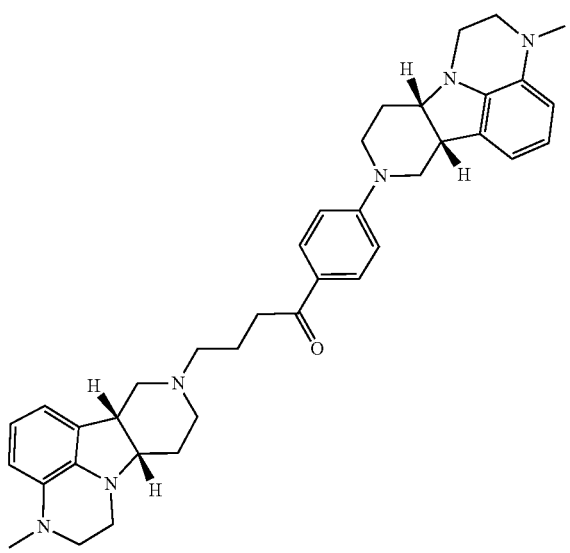 [SMILES: CN1CCN2c3c(cccc31)[C@@H]1CN(CCCC(=O)c3ccc(N4CC[C@H]5[C@@H](C4)c4cccc6c4N5CCN6C)cc3)CC[C@@H]12]

The compound of the present disclosure has been unexpectedly found to have potent affinity for, or activity at, serotonin receptors (e.g., 5-HT$_{2A}$, 5-HT$_{2B}$), serotonin transporters (SERT), dopamine receptors (e.g., D2), sodium channels (e.g., via site 2 binding), and norepinephrine transporters. This compound has been disclosed as synthetic by-product in the synthesis of lumateperone, e.g., in WO2019/241278 and US 2020/0102309, the contents of which are hereby incorporated by reference in its entirety.

In a first aspect, the present disclosure provides the compound (Compound 1) of Formula I:

Formula I

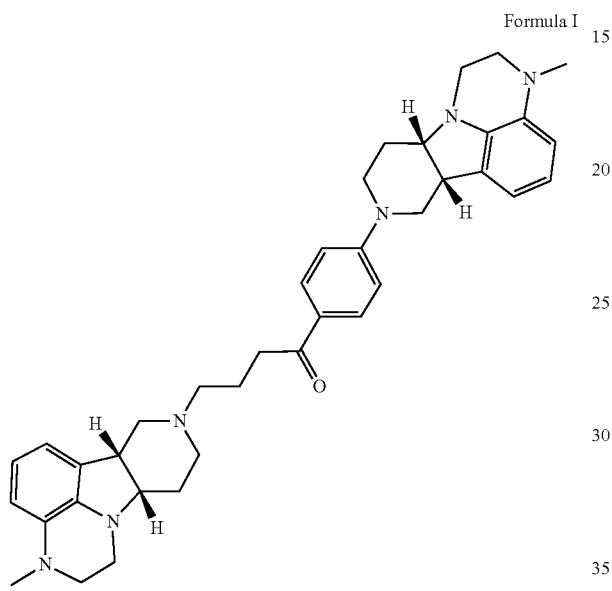

in free or salt form (e.g., pharmaceutically acceptable salt form), for example in an isolated or purified free or salt form.

The present disclosure provides additional exemplary embodiments of the Compound of Formula I, in free or salt form, for example in an isolated or purified free or salt form, including:

1.1 Compound 1 in free form (i.e., free base form);
1.2 Compound 1 in salt form, e.g., pharmaceutically acceptable salt form;
1.3 Compound 1.2, wherein the salt is an acid addition salt selected from hydrochloric, hydrobromic, sulfuric, sulfamic, phosphoric, nitric, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like;
1.4 Compound 1.3, in toluenesulfonic acid addition salt form, e.g., as a monotosylate salt, ditosylate salt, tritosylate salt, or tetratosylate salt, or any combination thereof;
1.5 Compound 1, or any of 1.1-1.4, in solid form;
1.6 Compound 1 or any of 1.1-1.5, in substantially pure diastereomeric form (i.e., substantially free from other diastereomers, including enantiomers);
1.7 Compound 1 or any of 1.1-1.6, having a diastereomeric excess of greater than 70%, preferably greater than 80%, more preferably greater than 90% and most preferably greater than 95%;
1.8 Compound 1 or any of 1.1-1.7 in isolated or purified form (e.g., in at least 90% pure form, or at least 95%, or at least 96%, or at least 97%, or at least 98%, or at least 99%);
1.9 Compound 1 or any of 1.1-1.8, wherein the compound has greater than 50% incorporation of deuterium at one or more of the hydrogen atom positions of the structure (i.e., greater than 50 atom % D), e.g., greater than 60%, or greater than 70%, or greater than 80%, or greater than 90% or greater than 95%, or greater than 96%, or greater than 97%, or greater than 98%, or greater than 99%;
1.10 Compound 1.9, wherein the Compound 1 is a compound of Formula:

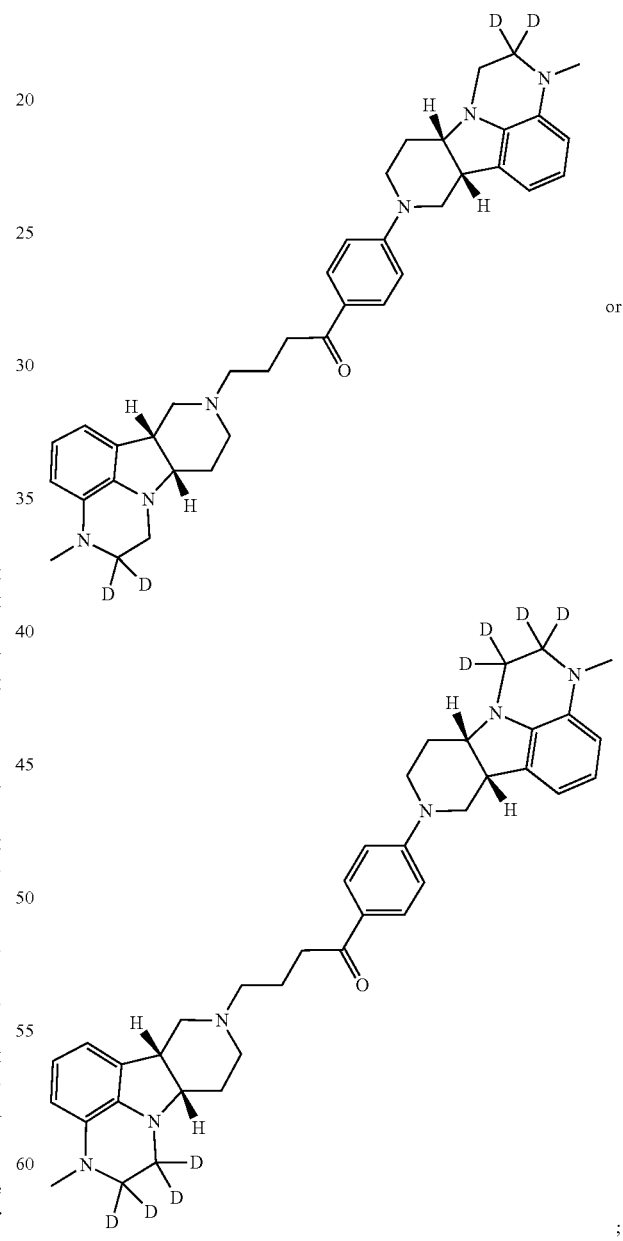

;

1.11 Compound 1.10, wherein D indicates an atomic position having at least 50% incorporation of deuterium, e.g., at least 60%, or at least 70%, or at least 80%, or at least 90% or at least 95%, or at least 96%, or at least 97%, or at least 98%, or at least 99%, up to 100 atom % deuterium.

In a second aspect, the present disclosure provides a pharmaceutical composition (Pharmaceutical Composition 2) comprising a Compound 1 or any of 1.1-1.11, e.g., in admixture with a pharmaceutically acceptable diluent or carrier. The present disclosure provides additional exemplary embodiments of Pharmaceutical Composition 2, including:

2.1 Pharmaceutical Composition 2, wherein the Compound of Formula 1 or any of 1.1-1.11 is in solid form;

2.2 Pharmaceutical Composition 2 or 2.1, wherein the compound of Formula 1 is in pharmaceutically acceptable salt form, e.g., a compound selected from Compound 1.3 or 1.4, or any of Compounds 1.5-1.11;

2.3 Pharmaceutical Composition 2 or any of 2.1 to 2.2, wherein the pharmaceutical composition further comprises the compound of Formula II:

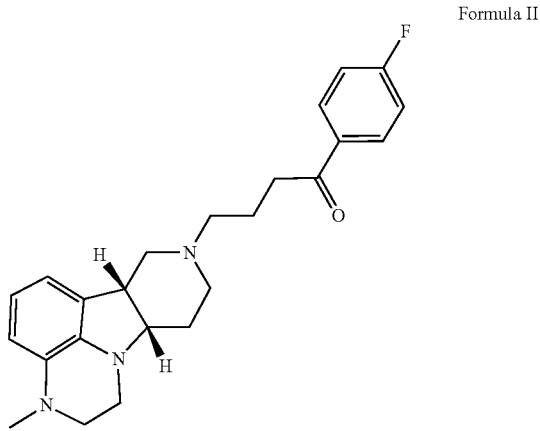 [SMILES: CN1CCN2c3c(cccc31)[C@@H]1CN(CCCC(=O)c3ccc(F)cc3)CC[C@@H]12]

Formula II in free or pharmaceutically acceptable salt form;

2.4 Pharmaceutical Composition 2.3, wherein the compound of Formula II is in pharmaceutically acceptable salt form, e.g., toluenesulfonic acid addition salt form (e.g., monotosylate or ditosylate salt form);

2.5 Pharmaceutical Composition 2.3 or 2.4, comprises the compound of Formula I and the compound of Formula II in a weight ratio of from 1:200 to 1:2000, e.g., 1:245 to 1:1000, or 1:250 to 1:550, or 1:285 to 1:460, or 1:300 to 1:500;

2.6 Pharmaceutical Composition 2 or any of 2.1 to 2.2, wherein the pharmaceutical composition does not comprise the compound of Formula II;

2.7 Pharmaceutical Composition 2 or any of 2.1-2.6, wherein the pharmaceutically acceptable diluent or carrier is selected from one or more of (a) diluent/filler (e.g., cellulose or microcrystalline cellulose (e.g., silicified microcrystalline cellulose), mannitol, lactose monohydrate, dicalcium phosphate, or isomalt), (b) binder (e.g., hydroxypropyl cellulose, hydroxypropyl methyl cellulose, copovidone), (c) disintegrant (e.g., sodium starch glycolate, crospovidone or croscarmellose sodium), (d) lubricant (e.g., magnesium stearate or glyceryl monostearate), (e) glidant (e.g., silicon dioxide or talc), (f) effervescent, (g) polymer, (h) plasticizer, (i) drying agent or desiccant, (j) humectant (e.g., polyol), (k) wetting agent, (l) anti-oxidant (e.g., BHT, citric acid, propyl gallate, ascorbic acid or sodium metabisulfite), (m) thickening agent (e.g., gelling agent), (n) surfactant, (o) buffer, (p) sweetener or flavor, and (q) dye or colorant, or any other agents as described in PCT/US2019/049061, PCT/US2019/049062 or U.S. Pat. No. 10,695,345, the contents of each of which are hereby incorporated by reference in their entireties.

In a preferred embodiment, the Pharmaceutical Composition of the present disclosure comprises a Compound of Formula 1 or 1.1-1.11, in free or pharmaceutically acceptable salt form, in admixture with a pharmaceutically acceptable diluent or carrier.

In a further embodiment, the Pharmaceutical Compositions of the present disclosure, are sustained or delayed release formulations, for example, depot formulations. In one embodiment, the depot formulation (Pharmaceutical Composition 2.8) is the Pharmaceutical Composition 2 or any of 2.1-2.7, preferably in free or pharmaceutically acceptable salt form, and preferably in admixture with a pharmaceutically acceptable diluent or carrier, e.g., providing sustained or delayed release as an injectable depot.

In a further embodiment, the present disclosure provides Pharmaceutical Composition 2.9, which is Pharmaceutical Composition 2 or any of 2.1-2.8, wherein the Compound of Formula 1 et seq. is in a polymeric matrix. In one embodiment, the Compound of the present disclosure is dispersed or dissolved within the polymeric matrix. In a further embodiment, the polymeric matrix comprises standard polymers used in depot formulations such as polymers selected from a polyester of a hydroxyfatty acid and derivatives thereof, or a polymer of an alkyl alpha-cyanoacrylate, a polyalkylene oxalate, a polyortho ester, a polycarbonate, a polyortho-carbonate, a polyamino acid, a hyaluronic acid ester, and mixtures thereof. In a further embodiment, the polymer is selected from a group consisting of polylactide, poly d,l-lactide, poly glycolide, PLGA 50:50, PLGA 85:15 and PLGA 90:10 polymer. In another embodiment, the polymer is selected form poly(glycolic acid), poly-D,L-lactic acid, poly-L-lactic acid, copolymers of the foregoing, poly(aliphatic carboxylic acids), copolyoxalates, polycaprolactone, polydioxanone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. In a preferred embodiment, the polymeric matrix comprises poly(d,l-lactide-co-glycolide).

For example, in one embodiment of Pharmaceutical Composition 2.9, the Compound is the Compound of Formula 1 or 1.1 et seq., in free or pharmaceutically acceptable salt form. In another example of Pharmaceutical Composition 2.9, the Compound is the Compound of Formula 1 or 1.1 et seq. in free or pharmaceutically acceptable salt form, in admixture with a pharmaceutically acceptable diluent or carrier. In another example of Pharmaceutical Composition 2.9, the Compound is the Compound of Formula 1 or 1.1 et seq., in admixture with a pharmaceutically acceptable diluent or carrier, wherein the diluent or carrier comprises a polymeric matrix, optionally wherein the polymeric matrix comprises a poly(d,l-lactide-co-glycolide) copolymer.

In some embodiments, Pharmaceutical Composition 2.9 is particularly useful for sustained or delayed release, wherein the Compound of the present disclosure is released upon degradation of the polymeric matrix. These Compositions may be formulated for controlled- and/or sustained-release of the Compounds of the present disclosure (e.g., as a depot composition) over a period of up to 180 days, e.g., from about 14 to about 30 to about 180 days. For example, the polymeric matrix may degrade and release the Compounds of the present disclosure over a period of about 30, about 60 or about 90 days. In another example, the polymeric matrix may degrade and release the Compounds of the present disclosure over a period of about 120, or about 180 days.

In still another embodiment, the Pharmaceutical Compositions of the present disclosure, for example the depot composition of the present disclosure, e.g., Pharmaceutical Composition 2.8, is formulated for administration by injection.

In further embodiment, the present disclosure provides the Compounds of Formulas 1 or 1.1 et seq. as hereinbefore described, in an osmotic controlled release oral delivery system (OROS), which is described U.S. Pub. No. 2009/0202631, the contents of which are incorporated by reference in its entirety. Therefore in one embodiment of the seventh aspect, the present disclosure provides a pharmaceutical composition or device comprising (a) a gelatin capsule containing a Compound of any of Formulas 1 or 1.1 et seq. in free or pharmaceutically acceptable salt form or a Pharmaceutical Composition of the Invention, as hereinbefore described; (b) a multilayer wall superposed on the gelatin capsule comprising, in outward order from the capsule: (i) a barrier layer, (ii) an expandable layer, and (iii) a semipermeable layer; and (c) and orifice formed or formable through the wall (Pharmaceutical Composition P.1).

In another embodiment, the invention provides a pharmaceutical composition comprising a gelatin capsule containing a liquid, the Compound of Formulas 1 or 1.1 et seq. in free or pharmaceutically acceptable salt form or a Pharmaceutical Composition of the Invention, e.g., any of Pharmaceutical Composition 2 or 2.1-2.9, the gelatin capsule being surrounded by a composite wall comprising a barrier layer contacting the external surface of the gelatin capsule, an expandable layer contacting the barrier layer, a semipermeable layer encompassing the expandable layer, and an exit orifice formed or formable in the wall (Pharmaceutical Composition P.2).

In still another embodiment, the invention provides a composition comprising a gelatin capsule containing a liquid, the Compound of Formulas 1 or 1.1 et seq. in free or pharmaceutically acceptable salt form or a Pharmaceutical Composition of the Invention, e.g., any of Pharmaceutical Composition 2 or 2.1-2.9, the gelatin capsule being surrounded by a composite wall comprising a barrier layer contacting the external surface of the gelatin capsule, an expandable layer contacting the barrier layer, a semipermeable layer encompassing the expandable layer, and an exit orifice formed or formable in the wall, wherein the barrier layer forms a seal between the expandable layer and the environment at the exit orifice (Pharmaceutical Composition P.3).

In still another embodiment, the invention provides a composition comprising a gelatin capsule containing a liquid, the Compound of Formulas 1 or 1.1 et seq. in free or pharmaceutically acceptable salt form or a Pharmaceutical Composition of the Invention, e.g., any of Pharmaceutical Composition 2 or 2.1-2.9, the gelatin capsule being surrounded by a barrier layer contacting the external surface of the gelatin capsule, an expandable layer contacting a portion of the barrier layer, a semi-permeable layer encompassing at least the expandable layer, and an exit orifice formed or formable in the dosage form extending from the external surface of the gelatin capsule to the environment of use (Pharmaceutical Composition P.4). The expandable layer may be formed in one or more discrete sections, such as for example, two sections located on opposing sides or ends of the gelatin capsule.

In a particular embodiment, the Compound of the present disclosure in the Osmotic-controlled Release Oral Delivery System (i.e., in Pharmaceutical Composition P.1-P.4) is in a liquid formulation, which formulation may be neat, liquid active agent, liquid active agent in a solution, suspension, emulsion or self-emulsifying composition or the like.

Further information on Osmotic-controlled Release Oral Delivery System composition including characteristics of the gelatin capsule, barrier layer, an expandable layer, a semi-permeable layer; and orifice may be found in US 2001/0036472, the contents of which are incorporated by reference in its entirety.

Other Osmotic-controlled Release Oral Delivery System for the Compound of 1 or 1.1 et seq. or the Pharmaceutical Composition of the present disclosure may be found in U.S. Pub. No. 2009/0202631, the contents of which are incorporated by reference in their entirety. Therefore, in another embodiment of the seventh aspect, the invention provides a composition or device comprising (a) two or more layers, said two or more layers comprising a first layer and a second layer, said first layer comprises the Compound of 1 or 1.1 et seq., in free or pharmaceutically acceptable salt form, or a Pharmaceutical Composition as herein before described said second layer comprises a polymer; (b) an outer wall surrounding said two or more layers; and (c) an orifice in said outer wall (Pharmaceutical Composition P.5).

Composition P.5 preferably utilizes a semi-permeable membrane surrounding a three-layer-core: in these embodiments the first layer is referred to as a first drug layer and contains low amounts of drug (e.g., the Compound of 1 or 1.1 et seq.) and an osmotic agent such as salt, the middle layer referred to as the second drug layer contains higher amounts of drug, excipients and no salt; and the third layer referred to as the push layer contains osmotic agents and no drug (Pharmaceutical Composition P.6). At least one orifice is drilled through the membrane on the first drug layer end of the capsule-shaped tablet.

Composition P.5 or P.6 may comprise a membrane defining a compartment, the membrane surrounding an inner protective subcoat, at least one exit orifice formed or formable therein and at least a portion of the membrane being semi-permeable; an expandable layer located within the compartment remote from the exit orifice and in fluid communication with the semi-permeable portion of the membrane; a first drug layer located adjacent the exit orifice; and a second drug layer located within the compartment between the first drug layer and the expandable layer, the drug layers comprising the Compound of the Invention in free or pharmaceutically acceptable salt thereof (Pharmaceutical Composition P.7). Depending upon the relative viscosity of the first drug layer and second drug layer, different release profiles are obtained. It is imperative to identify the optimum viscosity for each layer. In the present invention, viscosity is modulated by addition of salt, sodium chloride. The delivery profile from the core is dependent on the weight, formulation and thickness of each of the drug layers.

In a particular embodiment, the invention provides Pharmaceutical Composition P.7 wherein the first drug layer comprising salt and the second drug layer containing no salt. Pharmaceutical Composition P.5-P.7 may optionally comprise a flow-promoting layer between the membrane and the drug layers.

Pharmaceutical Compositions P.1-P.7 may generally be referred to as Osmotic-controlled Release Oral Delivery System Composition.

In a third aspect, the invention provides a method (Method 3) for the treatment or prophylaxis of a central nervous system disorder or cardiac disorder, comprising administering to a patient in need thereof a Compound of 1 or 1.1 et seq. or a Pharmaceutical Composition 2 or 2.1-2.9 or P.1-P.7.

In a further embodiment of the third aspect, the present disclosure provides Method 3, wherein the method is further as described as follows:

3.1 Method 3, wherein the central nervous system disorder is a disorder involving the serotonin 5-HT$_2$ receptor (e.g., 5-HT$_{2A}$ or 5-HT$_{2B}$), dopamine D2 receptor system, the serotonin reuptake transporter (SERT), the norepinephrine reuptake transported (NET), and/or the sodium ion channel (e.g., voltage gated sodium channel), for example, as similarly described in US 2011/071080, the contents of which are herein incorporated by reference in its entirety;

3.2 Method 3 or 3.1, wherein the central nervous system disorder is a disorder selected from the group consisting of obesity, anxiety, depression (for example refractory depression and/or MDD (major depressive disorder)), psychosis (including psychosis associated with dementia, such as hallucinations in advanced Parkinson's disease or paranoid delusions), schizophrenia, sleep disorders (particularly sleep disorders associated with schizophrenia and other psychiatric and neurological diseases), sexual disorders, migraine, conditions associated with cephalic pain, social phobias, agitation in dementia (e.g., agitation in Alzheimer's disease), agitation in autism and related autistic disorders, gastrointestinal disorders such as dysfunction of the gastrointestinal tract motility, and dementia, for example dementia of Alzheimer's disease or of Parkinson's disease; and mood disorders; obsessive-compulsive disorder (OCD), obsessive-compulsive personality disorder (OCPD), general anxiety disorder, social anxiety disorder, panic disorder, agoraphobia, compulsive gambling disorder, compulsive eating disorder, body dysmorphic disorder, hypochondriasis, pathological grooming disorder, kleptomania, pyromania; attention deficit-hyperactivity disorder (ADHD), attention deficit disorder (ADD), impulse control disorder; neurodegenerative disorders (e.g., Alzheimer's disease or Parkinson's disease), orthostatic intolerance, pain disorders (e.g., neuropathic pain, traumatic pain), substance abuse disorders, and combination thereof;

3.3 Method 3 or 3.1, wherein the central nervous system disorder is a disorder selected from the following: (i) psychosis, e.g., schizophrenia, in a patient suffering from depression; (2) depression in a patient suffering from psychosis, e.g., schizophrenia; (3) mood disorders associated with psychosis, e.g., schizophrenia or Parkinson's disease; (4) sleep disorders associated with psychosis, e.g., schizophrenia or Parkinson's disease; ad (5) substance a use disorders and/or substance-induced disorders, optionally wherein the patient suffers from residual symptoms of anxiety or anxiety disorder;

3.4 Method 3 or 3.1, wherein the central nervous system disorder is psychosis, e.g., schizophrenia and said patient is a patient suffering from depression;

3.5 Method 3 or 3.1, wherein the central nervous system disorder is selected from obsessive-compulsive disorder (OCD), obsessive-compulsive personality disorder (OCPD), social anxiety disorder, panic disorder, agoraphobia, compulsive gambling disorder, compulsive eating disorder, body dysmorphic disorder and impulse control disorder;

3.6 Method 3 or 3.1, wherein the central nervous system disorder is obsessive-compulsive disorder (OCD) or obsessive-compulsive personality disorder (OCPD);

3.7 Method 3 or 3.1, wherein said central nervous system disorder is depression and said patient is a patient suffering from psychosis, e.g., schizophrenia, or Parkinson's disease;

3.8 Method 3 or 3.1, wherein the central nervous system disorder is a sleep disorder;

3.9 Method 3.8, wherein said sleep disorder is sleep maintenance insomnia, frequent awakening, and/or waking up feeling unrefreshed;

3.10 Method 3.7 or 3.8, wherein the patient is also suffering from depression;

3.11 Method 3.7, 3.8 or 3.9, wherein said patient is also suffering from psychosis, e.g., schizophrenia;

3.12 Method 3.7-3.11, wherein said patient is also suffering from Parkinson's disease;

3.13 Method 3 or 3.1, wherein the central nervous system disorder is depression, anxiety or a combination thereof;

3.14 Method 3.13, wherein the depression and/or anxiety is acute depression and/or acute anxiety;

3.15 Any of methods 3.13-3.14, wherein the central nervous system disorder is acute anxiety (e.g., a short-duration anxious episode associated with generalized anxiety disorder, panic disorder, specific phobias, or social anxiety disorder, or social avoidance);

3.16 Any of methods 3.13-3.15, wherein the central nervous system disorder is acute depression (e.g., acute major depressive episode, acute short-duration depressive episode, acute recurrent brief depressive episode);

3.17 Any of methods 3.13-3.16, wherein the central nervous system disorder is treatment resistant depression (e.g., depression which has not responded to treatment with an antidepressant agent selected from a selective serotonin reuptake inhibitor (SSRI), a serotonin reuptake inhibitor (SRI), a tricyclic antidepressant, a monoamine oxidase inhibitor, a norepinephrine reuptake inhibitor (NRI), a dopamine reuptake inhibitor (DRI), an SRI/NRI, an SRI/DRI, an NRI/DRI, an SRI/NRI/DRI (triple reuptake inhibitor), a serotonin receptor antagonist, or any combination thereof);

3.18 Any of Methods 3.13-3.17, wherein the central nervous system disorder is selected from bipolar depression and major depressive disorder;

3.19 Any foregoing method, wherein said patient is not responsive to or cannot tolerate the side effects from, treatment with selective serotonin reuptake inhibitors (SSRIs), such as citalopram, escitalopram, fluoxetine, fluvoxamine, paroxetine, and sertraline;

3.20 Any foregoing method, wherein said patient is not responsive to or cannot tolerate the side effects from, treatment with serotonin-norepinephrine reuptake inhibitors (SNRIs), such as venlafaxine, sibutramine, duloxetine, atomoxetine, desvenlafaxine, milnacipran, and levomilnacipran;

3.21 Any foregoing method, wherein said patient is not responsive to or cannot tolerate the side effects from, treatment with antipsychotic agents, such as clomipramine, risperidone, quetiapine and olanzapine;

3.22 Any foregoing method, wherein said patient is unable to tolerate the side effects of conventional antipsychotic drugs, e.g., chlorpromazine, haloperidol, droperidol, fluphenazine, loxapine, mesoridazine molindone, perphenazine, pimozide, prochlorperazine promazine, thioridazine, thiothixene, trifluoperazine, clozapine, aripiprazole, olanzapine, quetiapine, risperidone and ziprasidone;

3.23 Any foregoing method, wherein said patient is unable to tolerate the side effects of conventional antipsychotic drugs, e.g., haloperidol, aripiprazole, clozapine, olanzapine, quetiapine, risperidone, and ziprasidone;

3.24 Any of the foregoing methods, wherein the effective amount is 1 mg-1000 mg, preferably 2.5 mg-50 mg;

3.25 Any of the foregoing methods, wherein the effective amount is 1 mg-100 mg per day, preferably 2.5 mg-50 mg per day;

3.26 Any of the foregoing methods wherein the central nervous system disorder is dyskinesia, e.g., in a patient receiving dopaminergic medications, e.g., medications selected from levodopa and levodopa adjuncts (carbidopa, COMT inhibitors, MAO-B inhibitors), dopamine agonists, and anticholinergics, e.g., levodopa;

3.27 Any of the foregoing methods wherein the central nervous system disorder is Parkinson's disease;

3.28 Any of the foregoing methods wherein the central nervous system disorder is Alzheimer's disease;

3.29 Any of the foregoing methods wherein the central nervous system disorder is a seizure disorder (e.g., epilepsy, generalized seizure disorder, status epilepticus);

3.30 Any of the foregoing methods wherein the central nervous system disorder is a pain disorder (e.g., acute pain, chronic pain, neuropathic pain and/or traumatic pain);

3.31 Method 3.30, wherein the patient is unable to tolerate the side effects from conventional analgesics, such as non-steroidal anti-inflammatory drugs (NSAIDS) (e.g., aspirin, ibuprofen, naproxen, acetaminophen) or wherein such analgesics are ineffective to treat the patient's pain;

3.32 Method 3.30 or 3.31, wherein the patient is unable to tolerate the side effects from narcotic analgesics, such as opiates and opioids (e.g., morphine codeine, oxycodone, hydrocodone, meperidine, fentanyl) or wherein such agents are ineffective to treat the patient's pain, or wherein such agents are contraindicated (e.g., due to addiction, risk of addiction, dependence, or tolerance, or drug-drug interactions);

3.33 Method 3, wherein the wherein the cardiac disorder is an arrhythmia (e.g., ventricular arrhythmia, recurrent atrial fibrillation, paroxysmal atrial fibrillation, Wolff-Parkinson-White syndrome, increased QT interval), ventricular tachycardia, recurrent tachyarrhythmias, or myocardial infarction;

3.34 Any of the foregoing methods wherein the method comprises administering the Compound of Formula 1 in free form;

3.35 Any of Methods 3.1 to 3.34, wherein the method comprises administering the Compound of Formula 1 in salt form, e.g., pharmaceutically acceptable salt form;

3.36 Any of Methods 3.1 to 3.34, wherein the method comprises administering any Compound of Formula 1 or 1.1 to 1.11;

3.37 Any preceding method, wherein the method comprises administering a pharmaceutical composition comprising the Compound of Formula 1 or any of 1.1 to 1.11, in admixture with a pharmaceutically acceptable diluent or carrier;

3.38 Method 3.37, wherein the pharmaceutical Composition is Pharmaceutical Composition 2, or any of 2.1-2.9 or any of P.1 to P.7;

3.39 Any preceding method wherein the method comprises administering the Compound of Formula 1 or any of 1.1-1.11 in a form formulated for controlled- and/or sustained-release of the Compound over a period of from about 14 days, about 30 to about 180 days, preferably over the period of about 30, about 60 or about 90 days;

3.40 Any foregoing method, wherein the method further comprises concurrent administration of one or more additional therapeutic agents, optionally wherein the dose of either the Compound of the present disclosure and/or the one or more additional therapeutic agents is provided at a lower dose compared to when said Compound or agent is used as monotherapy.

The Compounds of the present disclosure, the Pharmaceutical Compositions of the present disclosure or the Depot Compositions of the present disclosure may be used in combination with a second therapeutic agent, particularly at lower dosages than when the individual agents are used as a monotherapy so as to enhance the therapeutic activities of the combined agents without causing the undesirable side effects commonly occur in conventional monotherapy. For example, the Compounds of the present disclosure may be simultaneously, sequentially, or contemporaneously administered with other anti-depressant, anti-psychotic, other hypnotic agents, and/or agents use to treat Parkinson's disease or mood disorders. In another example, side effects may be reduced or minimized by administering a Compound of the present disclosure in combination with one or more second therapeutic agents in free or salt form, wherein the dosages of (i) the second therapeutic agent(s) or (ii) both Compound of the present disclosure and the second therapeutic agents, are lower than if the agents/compounds are administered as a monotherapy. In a particular embodiment, the Compounds of the present disclosure are useful to treat dyskinesia in a patient receiving dopaminergic medications, e.g., selected from levodopa and levodopa adjuncts (carbidopa, COMT inhibitors, MAO-B inhibitors), dopamine agonists, and anticholinergics, e.g., such as are used in the treatment of Parkinson's disease.

In some further embodiments of the present disclosure, the Pharmaceutical Compositions of the present disclosure or the Depot Compositions of the present disclosure may be used in combination with a second therapeutic agent, particularly at lower dosages than when the individual agents are used as a monotherapy so as to enhance the therapeutic activities of the combined agents without causing the undesirable side effects.

The Compounds of the present disclosure may be simultaneously, sequentially, or contemporaneously administered with any such additional therapeutic agents.

In further embodiments of the third aspect, the invention provides:

3.41 Method 3.40, wherein the one or more therapeutic agents are selected from compounds that modulate GABA activity (e.g., enhances the activity and facilitates GABA transmission), a GABA-B agonist, a 5-HT receptor modulator (e.g., a 5-HT$_{1A}$ agonist, a 5-HT$_{2A}$ antagonist, a 5-HT$_{2A}$ inverse agonist, etc.), a melatonin receptor agonist, an ion channel modulator (e.g., blocker), a serotonin-2 antagonist/reuptake inhibitor (SARIs), an orexin receptor antagonist, an H3 agonist or antagonist, a noradrenergic agonist or antagonist, a galanin agonist, a CRH antagonist, human growth hormone, a growth hormone agonist, estrogen, an estrogen agonist, a neurokinin-1 drug, an anti-depressant, an opiate agonist and/or partial opiate agonist, an opiate antagonist and/or opiate inverse agonist, and an antipsychotic agent, e.g., an atypical antipsychotic agent, in free or pharmaceutically acceptable salt form;

3.42 Method 3.40, wherein the therapeutic agent(s) is compounds that modulate GABA activity (e.g., enhances the activity and facilitates GABA transmission);

3.43 Method 3.42, wherein the GABA compound is selected from a group consisting of one or more of doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gaboxadol, vigabatrin, tiagabine, EVT 201 (Evotec Pharmaceuticals) and estazolam;

3.44 Method 3.40, wherein the therapeutic agent is an additional 5HT2a antagonist;

3.45 Method 3.44, wherein said additional 5HT2a antagonist is selected from one or more of ketanserin, risperidone, eplivanserin, volinanserin (Sanofi-Aventis, France), pruvanserin, MDL 100907 (Sanofi-Aventis, France), HY 10275 (Eli Lilly), APD 125 (Arena Pharmaceuticals, San Diego, CA), and AVE8488 (Sanofi-Aventis, France);

3.46 Method 3.40, wherein the therapeutic agent is a melatonin receptor agonist;

3.47 Method 3.46, wherein the melatonin receptor agonist is selected from a group consisting of one or more of melatonin, ramelteon (ROZEREM®, Takeda Pharmaceuticals, Japan), VEC-162 (Vanda Pharmaceuticals, Rockville, MD), PD-6735 (Phase II Discovery) and agomelatine;

3.48 Method 3.40, wherein the therapeutic agent is an ion channel blocker;

3.49 Method 3.48, wherein said ion channel blocker is one or more of lamotrigine, gabapentin and pregabalin;

3.50 Method 3.40, wherein the therapeutic agent is an orexin receptor antagonist;

3.51 Method 3.50, wherein the orexin receptor antagonist is selected from a group consisting of orexin, a 1,3-biarylurea, SB-334867-a (GlaxoSmithKline, UK), GW649868 (GlaxoSmithKline) and a benzamide derivative;

3.52 Method 3.40, wherein the therapeutic agent is a serotonin-2 antagonist/reuptake inhibitor (SARI);

3.53 Method 3.52, wherein the serotonin-2 antagonist/reuptake inhibitor (SARI) is selected from a group consisting of one or more Org 50081 (Organon-Netherlands), ritanserin, nefazodone, serzone and trazodone;

3.54 Method 3.40, wherein the therapeutic agent is a 5HTIa agonist;

3.55 Method 3.54, wherein the 5HTIa agonist is selected from a group consisting of one or more of repinotan, sarizotan, eptapirone, buspirone and MN-305 (Medici-Nova, San Diego, CA);

3.56 Method 3.40, wherein the therapeutic agent is a neurokinin-1 drug;

3.57 Method 3.56, wherein the neurokinin-1 drug is Casopitant (GlaxoSmithKline);

3.58 Method 3.40, wherein the therapeutic agent is an antipsychotic agent;

3.59 Method 3.58, wherein the antipsychotic agent is selected from a group consisting of chlorpromazine, haloperidol, droperidol, fluphenazine, loxapine, mesoridazine, molindone, perphenazine, pimozide, prochlorperazine promazine, thioridazine, thiothixene, trifluoperazine, clozapine, aripiprazole, olanzapine, quetiapine, risperidone, ziprasidone and paliperidone;

3.60 Method 3.40, wherein the therapeutic agent is an anti-depressant;

3.61 Method 3.60, wherein the anti-depressant is selected from amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelzine sulfate, protriptyline, sertraline, tranylcypromine, trazodone, trimipramine, and venlafaxine;

3.62 Method 3.40, wherein the antipsychotic agent is an atypical antipsychotic agent;

3.63 Method 3.62, wherein the atypical antipsychotic agent is selected from a group consisting of clozapine, aripiprazole, olanzapine, quetiapine, risperidone, ziprasidone, and paliperidone;

3.64 Method 3.40, wherein the therapeutic agent is selected from the group consisting of modafinil, armodafinil, doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gaboxadol, vigabatrin, tiagabine, EVT 201 (Evotec Pharmaceuticals), estazolam, ketanserin, risperidone, eplivanserin, volinanserin (Sanofi-Aventis, France), pruvanserin, MDL 100907 (Sanofi-Aventis, France), HY 10275 (Eli Lilly), APD 125 (Arena Pharmaceuticals, San Diego, CA), AVE8488 (Sanofi-Aventis, France), repinotan, sarizotan, eptapirone, buspirone, MN-305 (Medici-Nova, San Diego, CA), melatonin, ramelteon (ROZEREM®, Takeda Pharmaceuticals, Japan), VEC-162 (Vanda Pharmaceuticals, Rockville, MD), PD-6735 (Phase 11 Discovery), agomelatine, lamotrigine, gabapentin, pregabalin, orexin, a 1,3-biarylurea, SB-334867-a (GlaxoSmithKline, UK), GW649868 (GlaxoSmithKline), a benzamide derivative, Org 50081 (Organon-Netherlands), ritanserin, nefazodone, serzone, trazodone, Casopitant (GlaxoSmithKline), amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelzine sulfate, protriptyline, sertraline, tranylcypromine, trazodone, trimipramine, venlafaxine, chlorpromazine, haloperidol, droperidol, fluphenazine, loxapine, mesoridazine, molindone, perphenazine, pimozide, prochlorperazine promazine, thioridazine, thiothixene, trifluoperazine, clozapine, aripiprazole, olanzapine, quetiapine, risperidone, ziprasidone and paliperidone;

3.65 Method 3.40, wherein the therapeutic agent is an H3 agonist;

3.66 Method 3.40, wherein the therapeutic agent is an H3 antagonist;

3.67 Method 3.40, wherein the therapeutic agent is a noradrenergic agonist or antagonist;
3.68 Method 3.40, wherein the therapeutic agent is a galanin agonist;
3.69 Method 3.40, wherein the therapeutic agent is a CRH antagonist;
3.70 Method 3.40, wherein the therapeutic agent is a human growth hormone;
3.71 Method 3.40, wherein the therapeutic agent is a growth hormone agonist;
3.72 Method 3.40, wherein the therapeutic agent is estrogen;
3.73 Method 3.40, wherein the therapeutic agent is an estrogen agonist;
3.74 Method 3.40, wherein the therapeutic agent is a neurokinin-1 drug;
3.75 Method 3.40, wherein the therapeutic agent is an anti-Parkinson agent such as L-dopa, co-careldopa, duodopa, stalevo, Symmetrel, benztropine, biperiden, bromocriptine, entacapone, pergolide, pramipexole, procyclidine, ropinirole, selegiline and tolcapone;
3.76 Method 3.40, wherein the therapeutic agent is an opiate agonist or partial opiate agonist, for example, a mu-agonist or partial agonist, or a kappa-agonist or partial agonist, including mixed agonist/antagonists (e.g., an agent with partial mu-agonist activity and kappa-antagonist activity);
3.77 Method 3.76, wherein the therapeutic agent is buprenorphine, optionally, wherein said method does not include co-treatment with an anxiolytic agent, e.g., a GABA compound or benzodiazepine;
3.78 Method 3.40, wherein the therapeutic agent(s) is an opiate receptor antagonist or inverse agonist, e.g., a full opiate antagonist, for example, selected from naloxone, naltrexone, nalmefene, methadone, nalorphine, levallorphan, samidorphan, nalodeine, cyprodime, or norbinaltorphimine;
3.79 Method 3.40, wherein the therapeutic agent is an anticonvulsant, antiarrhythmic (e.g., Class I, Class II or Class III antiarrhythmic), or an anesthetic;
3.80 Any of the foregoing methods, wherein the patient undergoes concurrent or consecutive treatment with lumateperone.

In another aspect of the invention, the combination of a Compound of the present disclosure (e.g., Compound 1 or any of 1.1-1.11) and one or more second therapeutic agents as described in Methods 3.38 to 3.80 may be administered to the patient as a Pharmaceutical Composition or a depot Composition as hereinbefore described. The combination compositions can include mixtures of the combined drugs, as well as two or more separate compositions of the drugs, which individual compositions can be, for example, co-administered together to a patient.

In a fourth aspect, the present disclosure provides for use of the Compound 1, or any of 1.1-1.11, or Pharmaceutical Composition 2, or any of 2.1-2.9, in Method 3 or any of Methods 3.1-3.80.

In a fifth aspect, the present disclosure provides for use of the Compound 1, or any of 1.1-1.11, or Pharmaceutical Composition 2, or any of 2.1-2.9, in the manufacture of a medicament for the treatment or prophylaxis of one or more central nervous system disorders as provided in any of Method 3 or 3.1-3.80.

In a sixth aspect, the present disclosure provides present disclosure Compound 1, or any of 1.1-1.11, or Pharmaceutical Composition 2, or any of 2.1-2.9, for use in Method 3 or any of 3.1-3.80.

DETAILED DESCRIPTION OF THE INVENTION

The words "treatment" and "treating" are to be understood accordingly as embracing prophylaxis and treatment or amelioration of symptoms of disease and/or treatment of the cause of the disease. In particular embodiments, the words "treatment" and "treating" refer to prophylaxis or amelioration of symptoms of the disease.

The term "patient" may include a human or non-human patient.

The Diagnostic and Statistical Manual of Mental Disorders, 5th Edition ("DSM-5"), defines "major depressive disorder" (MDD) as having five or more of a set of symptoms during the same two-week period of time, which symptoms represent a change from the patient's previous functioning. The five symptoms are selected from depressed mood, markedly diminished interest or pleasure in almost all activities, significant weight changes, insomnia or hyposomnia, psychomotor agitation or retardation, fatigue, feelings of worthlessness or excessive guilt, diminished ability to think or indecisiveness, and recurrent thoughts of death or suicidal ideation, wherein each of such symptoms is present nearly every day. At a minimum, MDD diagnosis requires at least depressed mood or loss of interest or pleasure as one of the five symptoms. MDD may consist of one or more "major depressive episodes" which can be spaced many weeks or months apart (more than 2 weeks apart to qualify as separate episodes). The DSM-5 notes that there is a risk of suicidal behavior at all time during a major depressive episode.

By its nature, MDD is an acute disorder in so far as the DSM-5 distinguishes it from "persistent depressive disorder", in which a patient has many of the same symptoms as for MDD, but which persists for at least a 2-year period. In addition to MDD, the DSM-5 also defines a "short-duration depressive episode" as having a depressed affect and at least four of the other symptoms which define MDD for at least 4 days, but less than 14 days. The DSM further defines "recurrent brief depression" as the concurrent presence of depressed mood and at least four other symptoms of depression for 2 to 13 days at least once per month, and persisting for at least 12 consecutive months. Thus, recurrent brief depression similarly consists of brief episodes of depression which recur regularly.

The DSM-5 also includes major depressive episodes as one of the diagnostic criteria for a patient suffering from bipolar disorder. Thus, a patient presenting a major depressive episode may be suffering from either major depressive disorder or bipolar disorder.

It is apparent that there are is a particular need for effective treatment of depression during the earliest stages of a major depressive episode, since each day of such episode can have profound consequences for a patient, yet typical SSRI anti-depressive agents take up to 2-4 weeks for beneficial effects to appear. The same is true for treatment of short duration depressive episodes as well as individual episodes of recurrent brief depression.

Thus, as used herein, the term "acute depression" refers to the initial period of what may be a brief or a chronic episode of depression (e.g., lasting 2 days to 2 weeks, or 2 weeks to 2 months, or 2 months to 2 years, or more). "Acute depression" may thus refer to the initial period of a major depressive episode, a short-duration depressive episode, or a recurrent brief depressive episode. There is a particular need in the art for the treatment of such acute stages of depressive episodes. A treatment initiated during this acute phase of depression may be continued indefinitely in those patients which respond thereto.

The DSM-5 defines a variety of anxiety disorders, including generalized anxiety disorder, panic disorder, social anxiety disorder, and specific phobias. Like the depressive disorders discussed above, anxiety disorders can be marked by recurrent episodes of short duration, such as panic attacks, which may persist over the course of a chronic disorder. For example, generalized anxiety disorder is defined by the DSM-5 to require excessive anxiety and worry occurring more days that not for at least 6 months, about a number of events or activities. A panic attack is defined as an abrupt surge of intense fear or intense discomfort that reaches a peak within minutes, but it can repeatedly recur in response to either expected stimuli or unexpected stimuli. Thus, as for the depressive disorders described above, there is a need for rapidly-acting anxiolytic agents that can treat the symptoms of anxiety or panic, yet some of the most common treatments for anxiety disorders are the SSRIs and other antidepressant agents which take 2-4 weeks to provide relief.

As used herein, "acute anxiety" refers to any short-duration episode of anxiety, e.g., lasting from one day or less to one week, which may be part of a chronic course of anxiety (e.g., lasting 2 days to 2 weeks, or 2 weeks to 2 months, or 2 months to 2 years, or more). "Acute anxiety" may thus include a panic attack or any specific instance of an anxious response to triggering stimuli or events (e.g., to the stimuli which trigger a specific phobia, the events which trigger social anxiety or generalized anxiety). There is a particular need in the art for the treatment of such acute stages of anxious episodes. A treatment initiated during this acute phase of anxiety may be continued indefinitely in those patients which respond thereto.

Social avoidance can be a critical and debilitating symptom in patients suffering from anxiety disorders, especially social anxiety disorder, as well as in patients suffering from traumatic anxiety disorders. Social avoidance is often one of the key determinants of whether a person with a severe anxiety disorder is capable of maintaining familial relationships or employment relationships. It has been unexpectedly found that certain substituted fused gamma carbolines having 5-$HT_{2A}$ and dopamine receptor activity, such as lumateperone, are effective in treating the emotional experience symptoms of psychiatric disorders (e.g., the emotional experience negative symptoms of schizophrenics). Negative symptoms of schizophrenia can be divided into two categories: emotional experience (e.g., emotional withdrawal, passive social withdrawal, active social avoidance) and emotional expression (e.g., blunted effect, poor rapport, lack of spontaneity, and motor retardation). In two clinical studies of patients with acute exacerbated schizophrenia, administration of lumateperone once daily (60 mg P.O.), for up to 28 days, resulted in a significant and unexpected improvement in symptoms of emotional experience compared to placebo. These are the symptoms that are most highly correlated with interpersonal functioning. As such, such compounds, including the compounds of Formula I, may be highly effective in treating the emotional experience symptoms of other psychiatric disorders, such as social anxiety disorders, or any other psychiatric disorders in which social withdrawal and social avoidance are symptoms.

Substance-use disorders and substance-induced disorders are the two categories of substance-related disorders defined by the Fifth Edition of the DSM (the Diagnostic and Statistical Manual of Mental Disorders, DSM-5). A substance-use disorder is a pattern of symptoms resulting from use of a substance which the individual continues to take, despite experiencing problems as a result. A substance-induced disorder is a disorder induced by use if the substance. Substance-induced disorders include intoxication, withdrawal, substance induced mental disorders, including substance induced psychosis, substance induced bipolar and related disorders, substance induced depressive disorders, substance induced anxiety disorders, substance induced obsessive-compulsive and related disorders, substance induced sleep disorders, substance induced sexual dysfunctions, substance induced delirium and substance induced neurocognitive disorders.

The DSM-5 includes criteria for classifying a substance use disorder as mild, moderate or severe. In some embodiments of the methods disclosed herein, the substance use disorder is selected from a mild substance use disorder, a moderate substance use disorder or a severe substance use disorder. In some embodiments, the substance use disorder is a mild substance use disorder. In some embodiments, the substance use disorder is a moderate substance use disorder. In some embodiments, the substance use disorder is a severe substance use disorder.

Anxiety and depression are highly prevalent co-morbid disorders in patients undergoing treatment of substance use or substance abuse.

If not otherwise specified or clear from context, the following terms as used herein have the following meetings:

The term "pharmaceutically acceptable diluent or carrier" is intended to mean diluents and carriers that are useful in pharmaceutical preparations, and that are free of substances that are allergenic, pyrogenic or pathogenic, and that are known to potentially cause or promote illness. Pharmaceutically acceptable diluents or carriers thus exclude bodily fluids such as example blood, urine, spinal fluid, saliva, and the like, as well as their constituent components such as blood cells and circulating proteins. Suitable pharmaceutically acceptable diluents and carriers can be found in any of several well-known treatises on pharmaceutical formulations, for example Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins, 2000; and Martindale, The Extra Pharmacopoeia, Thirty-Second Edition (The Pharmaceutical Press, London, 1999); all of which are incorporated by reference herein in their entirety.

The terms "purified," "in purified form" or "in isolated and purified form" for a compound refers to the physical state of said compound after being isolated from a synthetic process (e.g., from a reaction mixture), or natural source or combination thereof. Thus, the term "purified," "in purified form" or "in isolated and purified form" for a compound refers to the physical state of said compound after being obtained from a purification process or processes described herein or well known to the skilled artisan (e.g., chromatography, recrystallization, LC-MS and LC-MS/MS techniques and the like), in sufficient purity to be characterizable by standard analytical techniques described herein or well known to the skilled artisan. Depending on the nature and use of the compound and the process or processes used for purification, the term "purified" may reflect an actual purity of, for example, at least 90% pure form, or at least 95%, or at least 96%, or at least 97%, or at least 98%, or at least 99%, or at least 99.5%, or at least 99.9%.

The term "concurrently" when referring to a therapeutic use means administration of two or more active ingredients to a patient as part of a regimen for the treatment of a disease or disorder, whether the two or more active agents are given at the same or different times or whether given by the same or different routes of administrations. Concurrent administration of the two or more active ingredients may be at different times on the same day, or on different dates or at different frequencies.

The term "simultaneously" when referring to a therapeutic use means administration of two or more active ingredients at or about the same time by the same route of administration.

The term "separately" when referring to a therapeutic use means administration of two or more active ingredients at or about the same time by different route of administration.

The Compounds of the present disclosure are intended for use as pharmaceuticals, therefore pharmaceutically acceptable salts are preferred. Salts which are unsuitable for pharmaceutical uses may be useful, for example, for the isolation or purification of free Compounds of the Invention and are therefore also included within the scope of the compounds of the present disclosure.

The Compounds of the present disclosure may comprise one or more chiral carbon atoms. The compounds thus exist in individual isomeric, e.g., enantiomeric or diastereomeric form or as mixtures of individual forms, e.g., racemic/diastereomeric mixtures. Any isomer may be present in which the asymmetric center is in the (R)-, (S)-, or (R,S)-configuration. The invention is to be understood as embracing both individual optically active isomers as well as mixtures (e.g., racemic/diastereomeric mixtures) thereof. Accordingly, the Compounds of the Invention may be a racemic mixture or it may be predominantly, e.g., in pure, or substantially pure, isomeric form, e.g., greater than 70% enantiomeric/diastereomeric excess ("ee"), preferably greater than 80% ee, more preferably greater than 90% ee, most preferably greater than 95% ee. The purification of said isomers and the separation of said isomeric mixtures may be accomplished by standard techniques known in the art (e.g., column chromatography, preparative TLC, preparative HPLC, simulated moving bed and the like).

Geometric isomers by nature of substituents about a double bond or a ring may be present in cis (Z) or trans (E) form, and both isomeric forms are encompassed within the scope of this invention.

It is also intended that the compounds of the present disclosure encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the compounds of the disclosure may be replaced with deuterium (a stable isotope which is non-radioactive). Examples of known stable isotopes include, but not limited to, deuterium, $^{13}C$, $^{15}N$, $^{18}O$. Alternatively, unstable isotopes, which are radioactive isotopes which contain additional neutrons compared to the abundant nuclides of the same species (i.e., element), e.g., $^{123}I$, $^{131}I$, $^{125}I$, $^{11}C$, $^{18}F$, may replace the corresponding abundant species of I, C and F. Another example of useful isotope of the compound of the invention is the $^{11}C$ isotope. These radio isotopes are useful for radio-imaging and/or pharmacokinetic studies of the compounds of the invention. In addition, the substitution of atoms of having the natural isotopic distributing with heavier isotopes can result in desirable change in pharmacokinetic rates when these substitutions are made at metabolically liable sites. For example, the incorporation of deuterium ($^2H$) in place of hydrogen can slow metabolic degradation when the position of the hydrogen is a site of enzymatic or metabolic activity.

The Compounds of the present disclosure may be included as a depot formulation, e.g., by dispersing, dissolving or encapsulating the Compounds of the Invention in a polymeric matrix as described herein, such that the Compound is continually released as the polymer degrades over time. The release of the Compounds of the Invention from the polymeric matrix provides for the controlled- and/or delayed- and/or sustained-release of the Compounds, e.g., from the pharmaceutical depot composition, into a subject, for example a warm-blooded animal such as man, to which the pharmaceutical depot is administered. Thus, the pharmaceutical depot delivers the Compounds of the Invention to the subject at concentrations effective for treatment of the particular disease or medical condition over a sustained period of time, e.g., 14-180 days, preferably about 30, about 60 or about 90 days.

Polymers useful for the polymeric matrix in the Composition of the Invention (e.g., Depot composition of the Invention) may include a polyester of a hydroxyfatty acid and derivatives thereof or other agents such as polylactic acid, polyglycolic acid, polycitric acid, polymalic acid, poly-beta.-hydroxybutyric acid, epsilon.-capro-lactone ring opening polymer, lactic acid-glycolic acid copolymer, 2-hydroxybutyric acid-glycolic acid copolymer, polylactic acid-polyethyleneglycol copolymer or polyglycolic acid-polyethyleneglycol copolymer), a polymer of an alkyl alpha-cyanoacrylate (for example poly(butyl 2-cyanoacrylate)), a polyalkylene oxalate (for example polytrimethylene oxalate or polytetramethylene oxalate), a polyortho ester, a polycarbonate (for example polyethylene carbonate or polyethylenepropylene carbonate), a polyortho-carbonate, a polyamino acid (for example poly-gamma.-L-alanine, poly-.gamma.-benzyl-L-glutamic acid or poly-y-methyl-L-glutamic acid), a hyaluronic acid ester, and the like, and one or more of these polymers can be used.

If the polymers are copolymers, they may be any of random, block and/or graft copolymers. When the above alpha-hydroxycarboxylic acids, hydroxydicarboxylic acids and hydroxytricarboxylic acids have optical activity in their molecules, any one of D-isomers, L-isomers and/or DL-isomers may be used. Among others, alpha-hydroxycarboxylic acid polymer (preferably lactic acid-glycolic acid polymer), its ester, poly-alpha-cyanoacrylic acid esters, etc. may be used, and lactic acid-glycolic acid copolymer (also referred to as poly(lactide-alpha-glycolide) or poly(lactic-co-glycolic acid), and hereinafter referred to as PLGA) are preferred. Thus, in one aspect the polymer useful for the polymeric matrix is PLGA. As used herein, the term PLGA includes polymers of lactic acid (also referred to as polylactide, poly(lactic acid), or PLA). Most preferably, the polymer is the biodegradable poly(d,l-lactide-co-glycolide) polymer.

In a preferred embodiment, the polymeric matrix of the invention is a biocompatible and biodegradable polymeric material. The term "biocompatible" is defined as a polymeric material that is not toxic, is not carcinogenic, and does not significantly induce inflammation in body tissues. The matrix material should be biodegradable wherein the polymeric material should degrade by bodily processes to products readily disposable by the body and should not accumulate in the body. The products of the biodegradation should also be biocompatible with the body in that the polymeric matrix is biocompatible with the body. Particular useful examples of polymeric matrix materials include poly (glycolic acid), poly-D,L-lactic acid, poly-L-lactic acid, copolymers of the foregoing, poly(aliphatic carboxylic acids), copolyoxalates, polycaprolactone, polydioxanone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. The preferred polymer for use in the practice of this invention is dl(polylactide-co-glycolide). It is preferred that the molar ratio of lactide to glycolide in such a copolymer be in the range of from about 75:25 to 50:50.

Useful PLGA polymers may have a weight-average molecular weight of from about 5,000 to 500,000 Daltons, preferably about 150,000 Daltons. Dependent on the rate of degradation to be achieved, different molecular weight of polymers may be used. For a diffusional mechanism of drug release, the polymer should remain intact until all of the drug is released from the polymeric matrix and then degrade. The drug can also be released from the polymeric matrix as the polymeric excipient bioerodes.

The PLGA may be prepared by any conventional method, or may be commercially available. For example, PLGA can be produced by ring-opening polymerization with a suitable catalyst from cyclic lactide, glycolide, etc. (see EP-0058481B2; Effects of polymerization variables on PLGA properties: molecular weight, composition and chain structure).

It is believed that PLGA is biodegradable by means of the degradation of the entire solid polymer composition, due to the break-down of hydrolysable and enzymatically cleavable ester linkages under biological conditions (for example in the presence of water and biological enzymes found in tissues of warm-blooded animals such as humans) to form lactic acid and glycolic acid. Both lactic acid and glycolic acid are water-soluble, non-toxic products of normal metabolism, which may further biodegrade to form carbon dioxide and water. In other words, PLGA is believed to degrade by means of hydrolysis of its ester groups in the presence of water, for example in the body of a warm-blooded animal such as man, to produce lactic acid and glycolic acid and create the acidic microclimate. Lactic and glycolic acid are by-products of various metabolic pathways in the body of a warm-blooded animal such as man under normal physiological conditions and therefore are well tolerated and produce minimal systemic toxicity.

In another embodiment, the polymeric matrix useful for the invention may comprise a star polymer wherein the structure of the polyester is star-shaped. These polyesters have a single polyol residue as a central moiety surrounded by acid residue chains. The polyol moiety may be, e. g., glucose or, e. g., mannitol. These esters are known and described in GB 2,145,422 and in U.S. Pat. No. 5,538,739, the contents of which are incorporated by reference.

The star polymers may be prepared using polyhydroxy compounds, e. g., polyol, e.g., glucose or mannitol as the initiator. The polyol contains at least 3 hydroxy groups and has a molecular weight of up to about 20,000 Daltons, with at least 1, preferably at least 2, e.g., as a mean 3 of the hydroxy groups of the polyol being in the form of ester groups, which contain polylactide or co-polylactide chains. The branched polyesters, e.g., poly (d, 1-lactide-co-glycolide) have a central glucose moiety having rays of linear polylactide chains.

The depot compositions of the invention (e.g., Compositions 6 and 6.1-6.10, in a polymer matrix) as hereinbefore described may comprise the polymer in the form of microparticles or nanoparticles, or in a liquid form, with the Compounds of the Invention dispersed or encapsulated therein. "Microparticles" is meant solid particles that contain the Compounds of the Invention either in solution or in solid form wherein such compound is dispersed or dissolved within the polymer that serves as the matrix of the particle. By an appropriate selection of polymeric materials, a microparticle formulation can be made in which the resulting microparticles exhibit both diffusional release and biodegradation release properties.

When the polymer is in the form of microparticles, the microparticles may be prepared using any appropriate method, such as by a solvent evaporation or solvent extraction method. For example, in the solvent evaporation method, the Compounds of the Invention and the polymer may be dissolved in a volatile organic solvent (for example a ketone such as acetone, a halogenated hydrocarbon such as chloroform or methylene chloride, a halogenated aromatic hydrocarbon, a cyclic ether such as dioxane, an ester such as ethyl acetate, a nitrile such as acetonitrile, or an alcohol such as ethanol) and dispersed in an aqueous phase containing a suitable emulsion stabilizer (for example polyvinyl alcohol, PVA). The organic solvent is then evaporated to provide microparticles with the Compounds of the Invention encapsulated therein. In the solvent extraction method, the Compounds of the Invention and polymer may be dissolved in a polar solvent (such as acetonitrile, dichloromethane, methanol, ethyl acetate or methyl formate) and then dispersed in an aqueous phase (such as a water/PVA solution). An emulsion is produced to provide microparticles with the Compounds of the Invention encapsulated therein. Spray drying is an alternative manufacturing technique for preparing the microparticles.

Another method for preparing the microparticles of the invention is also described in both U.S. Pat. Nos. 4,389,330 and 4,530,840.

The microparticle of the present invention can be prepared by any method capable of producing microparticles in a size range acceptable for use in an injectable composition. One preferred method of preparation is that described in U.S. Pat. No. 4,389,330. In this method the active agent is dissolved or dispersed in an appropriate solvent. To the agent-containing medium is added the polymeric matrix material in an amount relative to the active ingredient that provides a product having the desired loading of active agent. Optionally, all of the ingredients of the microparticle product can be blended in the solvent medium together.

Solvents for the Compounds of the Invention and the polymeric matrix material that can be employed in the practice of the present invention include organic solvents, such as acetone; halogenated hydrocarbons, such as chloroform, methylene chloride, and the like; aromatic hydrocarbon compounds; halogenated aromatic hydrocarbon compounds; cyclic ethers; alcohols, such as, benzyl alcohol; ethyl acetate; and the like. In one embodiment, the solvent for use in the practice of the present invention may be a mixture of benzyl alcohol and ethyl acetate. Further information for the preparation of microparticles useful for the invention can be found in U.S. Patent Pub. No. 2008/0069885, the contents of which are incorporated herein by reference in their entirety.

The amount of the Compounds of the present disclosure incorporated in the microparticles usually ranges from about 1 wt % to about 90 wt. %, preferably 30 to 50 wt. %, more preferably 35 to 40 wt. %. By weight % is meant parts of the Compounds of the present disclosure per total weight of microparticle.

The pharmaceutical depot compositions may comprise a pharmaceutically-acceptable diluent or carrier, such as a water miscible diluent or carrier.

Details of Osmotic-controlled Release Oral Delivery System composition may be found in U.S. Pub. No. 2009/0202631, the contents of which are incorporated by reference in its entirety.

A "therapeutically effective amount" is any amount of the Compounds of the invention (for example as contained in the pharmaceutical depot) which, when administered to a subject suffering from a disease or disorder, is effective to cause a reduction, remission, or regression of the disease or disorder over the period of time as intended for the treatment.

Dosages employed in practicing the present invention will of course vary depending, e.g., on the particular disease or condition to be treated, the particular Compound of the Invention used, the mode of administration, and the therapy desired. Unless otherwise indicated, an amount of the Compound of the Invention for administration (whether administered as a free base or as a salt form) refers to or is based on the amount of the Compound of the Invention in free base form (i.e., the calculation of the amount is based on the free base amount).

Compounds of the Invention may be administered by any satisfactory route, including orally, parenterally (intravenously, intramuscular or subcutaneous) or transdermally, but are preferably administered orally. In certain embodiments, the Compounds of the Invention, e.g., in depot formulation, are preferably administered parenterally, e.g., by injection.

In general, satisfactory results for Method 3 et seq., as set forth above, are indicated to be obtained on oral administration at dosages of the order from about 1 mg to 100 mg once daily, preferably 2.5 mg-50 mg, e.g., 2.5 mg, 5 mg, 10 mg, 20 mg, 30 mg, 40 mg or 50 mg, once daily, preferably via oral administration. In some embodiments, particularly related to sleep disorders, satisfactory results are obtained on oral administration of dosages of the order from about 2.5 mg-5 mg, e.g., 2.5 mg, 3 mg, 4 mg or 5 mg, of a Compound of the Invention, in free or pharmaceutically acceptable salt form, once daily, preferably via oral administration.

For treatment of the disorders disclosed herein wherein the depot composition is used to achieve longer duration of action, the dosages will be higher relative to the shorter action composition, e.g., higher than 1-100 mg, e.g., 25 mg, 50 mg, 100 mg, 500 mg, 1,000 mg, or greater than 1000 mg. Duration of action of the Compounds of the present disclosure may be controlled by manipulation of the polymer composition, i.e., the polymer:drug ratio and microparticle size. Wherein the composition of the invention is a depot composition, administration by injection is preferred.

The pharmaceutically acceptable salts of the Compounds of the present disclosure can be synthesized from the parent compound which contains a basic or acidic moiety by conventional chemical methods. Generally, such salts can be prepared by reacting the free base forms of these compounds with a stoichiometric amount of the appropriate acid in water or in an organic solvent, or in a mixture of the two; generally, non-aqueous media like ether, ethyl acetate, ethanol, isopropanol, or acetonitrile are preferred.

Pharmaceutical compositions comprising Compounds of the present disclosure may be prepared using conventional diluents or excipients (an example include, but is not limited to sesame oil) and techniques known in the galenic art. Thus, oral dosage forms may include tablets, capsules, solutions, suspensions and the like.

The prior art discloses numerous synthetic methods applicable generally to fused heterocycle gamma-carbolines related to the compounds disclosed herein. The skilled artisan may follow or adapt procedures as variously described in U.S. Pat. RE39,680; U.S. Pat. Nos. 7,183,282; 8,309,722; 9,751,883; and U.S. Patent Pub. 2017/0319580.

Diastereomers of prepared compounds can be separated by, for example, HPLC using CHIRALPAK® AY-H, 5 µ, 30×250 mm at room temperature and eluted with 10% ethanol/90% hexane/0.1% dimethylethylamine. Peaks can be detected at 230 nm to produce 98-99.9% ee of the diastereomer.

Example 1: Synthesis of 4-((6bR,10aS)-3-methyl-2,3,6b,9,10,10a-hexahydro-1H-pyrido[3',4':4,5]pyrrolo[1,2,3-de]quinoxalin-8(7H)-yl)-1-(4-((6bR,10aS)-3-methyl-2,3,6b,9,10,10a-hexahydro-1H-pyrido[3',4':4,5]pyrrolo[1,2,3-de]quinoxalin-8(7H)-yl)phenyl)butan-1-one

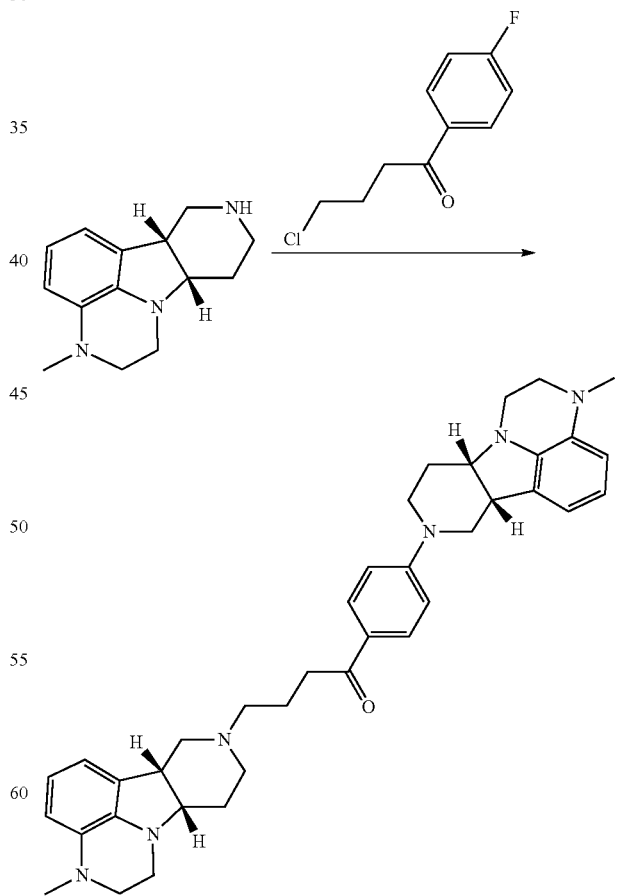

A suspension of (6bR,10aS)-3-methyl-2,3,6b,7,8,9,10,10a-octahydro-1H-pyrido-[3',4':4,5]-pyrrolo[1,2,3-de]quinoxaline (ca. 11.8 g, ca. 50 mmol), 4-chloro-4'-fluorobutyrophenone (15.0 g, 74.8 mmol), triethylamine (30 mL, 214 mmol), and potassium iodide (12.6 g, 76 mmol) in dioxane (65 ml) and toluene (65 ml) is heated to reflux for 7 hours. After filtration and evaporation of the solvent, 200 ml of DCM is added. The DCM solution is washed with brine, dried ($Na_2SO_4$) and concentrated to approximately 55 ml. The concentrated solution is added dropwise to 600 ml of 0.5N HCl in ether solution. The solid is filtered off and washed with ether and then dissolved in water. The resulting aqueous solution is basified with 2N NaOH and extracted with DCM. The DCM layers are combined, washed with brine (2×200 mL) and dried ($Na_2SO_4$). Evaporation of the solvent and chromatography of the residue over silica gel gives the title product.

Example 2: Receptor Binding Profile of Compound of Examples 1

Receptor binding is determined for the Compounds of Example 1. The following literature procedures are used, each of which reference is incorporated herein by reference in their entireties: $5\text{-}HT_{2A}$: Bryant, H. U. et al. (1996), *Life Sci.*, 15:1259-1268; D2: Hall, D. A. and Strange, P. G. (1997), *Brit. J. Pharmacol.*, 121:731-736; D1: Zhou, Q. Y. et al. (1990), *Nature*, 347:76-80; SERT: Park, Y. M. et al. (1999), *Anal. Biochem.*, 269:94-104; Mu opiate receptor: Wang, J. B. et al. (1994), *FEBS Lett.*, 338:217-222.

The compound of Example 1 is tested at a concentration of 1.0 µM in DMSO solution. Compound binding is calculated as the percent inhibition of the binding of a radioactively labeled ligand specific for each target. The control ligands are radiolabeled forms of SCH 23390 (for D1), 7-hydroxy-DPAT (for D2S), racemic DOI (for $5\text{-}HT_{2A}$ and $5\text{-}HT_{2B}$), veratridine (for sodium channel site 2), protriptyline (for NET) and imipramine (for SERT).

In general, the results are expressed as a percent of control specific binding:

$$\frac{\text{measured specific binding}}{\text{control specific binding}} \times 100$$

and as a percent inhibition of control specific binding:

$$100 - \left(\frac{\text{measured specific binding}}{\text{control specific binding}} \times 100\right)$$

obtained in the presence of the test compound (compound of Example 1).

The following receptor affinity results are obtained (% inhibition):

| Receptor | Compound 1 (Ex. 1) |
| --- | --- |
| SERT (antagonist binding) | 99.9% |
| $5\text{-}HT_{2A}$ (agonist binding) | 90.8% |
| $5\text{-}HT_{2B}$ (agonist binding) | 87.0% |
| D2S (agonist binding) | 80.63% |
| D1 (antagonist binding) | 52.3% |
| Sodium channel (site 2 antagonist binding) | 87.0% |
| NET (antagonist binding) | 82.9% |

These results show that the compound of the present disclosure has a unique and unexpected receptor binding profile.

Further pharmacology studies are conducted to determine $IC_{50}$ values for receptor binding to the $5\text{-}HT_{2A}$ receptor, D1 receptor, and SERT. For each study, the compound of Example 1 is tested at a range of concentrations and compound binding at each concentration is calculated as the percent inhibition of the binding of a radioactively labeled ligand specific for the target. The control ligands are radiolabeled forms of 7-hydroxy-DPAT (for D2S), racemic DOI (for $5\text{-}HT_{2A}$), and imipramine (for SERT). The $IC_{50}$ value is determined by non-linear regression analysis of the competition curve generated with mean replicate values using Hill Equation curve fitting:

$$Y = D + \frac{[A-D]}{1+(C/IC_{50})^{nH}}$$

wherein Y is specific binding, A is the left asymptote of the curve, D is the right asymptote of the curve, C is the compound concentration, and nH is the slope factor. $K_i$ values are calculated using the Cheng Prusoff equation:

$$K_i = \frac{IC_{50}}{(1+L/K_D)}$$

wherein L is the concentration of the radioligand in the assay, and $K_D$ is the affinity of the radioligand for the receptor. A scatchard plot is used to determine the $K_D$.

Using the above methods, the following $K_i$ and $IC_{50}$ results are obtained:

| Receptor | Compound 1 (Ex. 1) $K_i$ | Compound 1 (Ex. 1) $IC_{50}$ |
| --- | --- | --- |
| SERT (antagonist binding) | 1.3 nM | 2.9 nM |
| $5\text{-}HT_{2A}$ (agonist binding) | 51 nM | 68 nM |
| D2S (agonist binding) | 72 nM | 180 nM |

These results show that the compound of the present disclosure has a unique and unexpected receptor binding profile.

What is claimed is:

1. A pharmaceutical composition comprising a pharmaceutically acceptable diluent or carrier in admixture with:
(i) a compound of Formula I:

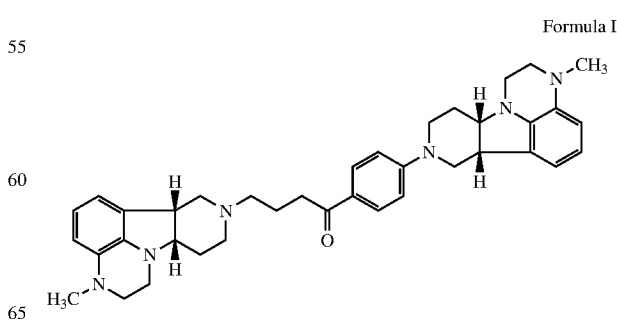

Formula I in free base or pharmaceutically acceptable salt form; and (ii) a compound of Formula II:

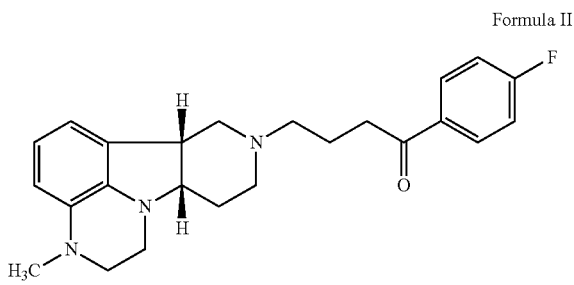 [SMILES: CN1CCN2c3c(cccc31)[C@@H]1CN(CCCC(=O)c3ccc(F)cc3)CC[C@@H]12]

Formula II in free base or pharmaceutically acceptable salt form.

2. The pharmaceutical composition according to claim 1, wherein the compound of Formula II is in toluenesulfonic acid addition salt form.

3. The pharmaceutical composition according to claim 2, wherein the pharmaceutical composition comprises the compound of Formula I and the compound of Formula II in a weight ratio in the range of from 1:200 to 1:2000.

4. The pharmaceutical composition according to claim 2, wherein the pharmaceutical composition comprises the compound of Formula I and the compound of Formula II in a weight ratio in the range of from 1:245 to 1:1000.

5. The pharmaceutical composition according to claim 2, wherein the pharmaceutical composition comprises the compound of Formula I and the compound of Formula II in a weight ratio in the range of from 1:250 to 1:550.

6. The pharmaceutical composition according to claim 2, wherein the pharmaceutical composition comprises the compound of Formula I and the compound of Formula II in a weight ratio in the range of from 1:300 to 1:500.

7. The pharmaceutical composition according to claim 2, wherein the pharmaceutical composition comprises the compound of Formula I and the compound of Formula II in a weight ratio in the range of from 1:285 to 1:400.

8. The pharmaceutical composition according to claim 1, wherein the pharmaceutical composition is formulated as a sustained release composition or delayed release composition.

9. The pharmaceutical composition according to claim 8, wherein the sustained release composition or delayed release composition is an injectable depot.

10. The pharmaceutical composition according to claim 1, wherein the pharmaceutical composition further comprises a polymeric matrix.

11. The pharmaceutical composition according to claim 10, wherein the polymeric matrix comprises a biodegradable poly(D,L-lactide-co-glycolide) polymer.

12. The pharmaceutical composition according to claim 11, wherein the polymeric matrix is comprised within a microsphere.

13. A method for (a) inhibiting serotonin (5-hydroxytryptamine) receptor activity, (b) modulating dopamine D2 receptor function, (c) inhibiting serotonin reuptake transporter activity, (d) inhibiting norepinephrine reuptake transporter activity, or (e) inhibiting sodium ion channel activity each in a patient in need thereof, wherein the method comprises administering to the patient a therapeutically effective amount of the pharmaceutical composition according to claim 1.

14. The method according to claim 13, wherein the patient has a cardiac disorder or a central nervous system disorder involving the serotonin (5-hydroxytryptamine) receptor, the dopamine D2 receptor system, the serotonin reuptake transporter, the norepinephrine reuptake transporter (NET), and/or the sodium ion channel.

15. The method according to claim 14, wherein the cardiac disorder is selected from the group consisting of an arrhythmia, myocardial infarction, a recurrent tachyarrhythmia, and a ventricular tachycardia.

16. The method according to claim 15, wherein the arrhythmia is selected from the group consisting of an increased QT interval, a paroxysmal atrial fibrillation, a recurrent atrial fibrillation, a ventricular arrhythmia, and Wolff-Parkinson-White syndrome.

17. The method according to claim 14, wherein the central nervous system disorder is selected from the group consisting of an agitation in autism, an agitation in dementia, agoraphobia, anxiety, attention deficit disorder, body dysmorphic disorder, compulsive eating disorder, compulsive gambling disorder, dementia, depression, a gastrointestinal disorder, hypochondriasis, impulse control disorder, kleptomania, migraine, a mood disorder, a neurodegenerative disorder, obesity, an obsessive-compulsive disorder, orthostatic intolerance, a pain disorder, pathological grooming disorder, psychosis, pyromania, schizophrenia, a seizure disorder, a sexual disorder, a sleep disorder, a social phobia, and a substance abuse disorder, or a combination thereof.

18. The method according to claim 17, wherein the central nervous system disorder is anxiety or depression, or a combination thereof.

19. The method according to claim 18, wherein the anxiety or depression is acute anxiety or acute depression.

20. The method according to claim 19, wherein the acute anxiety is selected from the group consisting of a short-duration anxious episode associated with generalized anxiety disorder, a short-duration anxious episode associated with panic disorder, a short-duration anxious episode associated with social anxiety disorder, a short-duration anxious episode associated with social avoidance, and a short-duration anxious episode associated with a specific phobia.

21. The method according to claim 19, wherein the acute depression is selected from the group consisting of an acute major depressive episode, an acute recurrent brief depressive episode, and an acute short-duration depressive episode.

22. The method according to claim 19, wherein the acute depression is treatment resistant depression.

23. The method according to claim 22, wherein the treatment resistant depression is depression which has not responded to treatment with an antidepressant agent selected from the group consisting of a dopamine reuptake inhibitor (DRI), a monoamine oxidase inhibitor, a norepinephrine reuptake inhibitor (NRI), a norepinephrine reuptake inhibitor/dopamine reuptake inhibitor (NRI/DRI), a serotonin receptor antagonist, a serotonin reuptake inhibitor (SRI), and a tricyclic antidepressant, or a combination thereof.

24. The method according to claim 23, wherein the serotonin reuptake inhibitor (SRI) is selected from the group consisting of a selective serotonin reuptake inhibitor (SSRI), a serotonin reuptake/dopamine reuptake inhibitor (SRI/DRI), a serotonin reuptake/norepinephrine reuptake inhibitor (SRI/NRI), and a serotonin reuptake/norepinephrine reuptake/dopamine reuptake inhibitor (SRI/NRI/DRI).

25. The method according to claim 17, wherein the central nervous system disorder is a pain disorder.

26. The method according to claim 17, wherein the central nervous system disorder is schizophrenia.

27. The method according to claim 17, wherein the central nervous system disorder is a seizure disorder.

28. The method according to claim 17, wherein the depression is bipolar depression or major depressive disorder.

29. A pharmaceutical composition comprising:
1) a compound of Formula I:

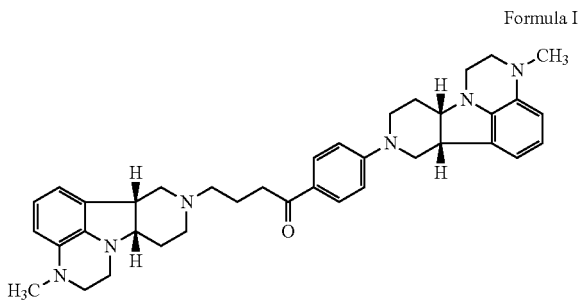 [SMILES: CN1CCN2c3c(cccc31)[C@@H]1CN(CCCC(=O)c3ccc(N4CC[C@H]5[C@@H](C4)c4cccc6c4N5CCN6C)cc3)CC[C@@H]12]

Formula I in free base or pharmaceutically acceptable salt form; and
(ii) a compound of Formula II:

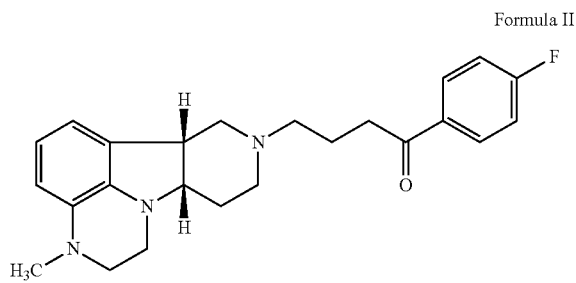 [SMILES: CN1CCN2c3c(cccc31)[C@@H]1CN(CCCC(=O)c3ccc(F)cc3)CC[C@@H]12]

Formula II in toluenesulfonic acid addition salt form;

wherein the pharmaceutical composition comprises the compound of Formula I and the compound of Formula II in a weight ratio in the range of from 1:200 to 1:2000.

30. The pharmaceutical composition according to claim 29, wherein the pharmaceutical composition comprises the compound of Formula I and the compound of Formula II in a weight ratio in the range of from 1:245 to 1:1000.

31. The pharmaceutical composition according to claim 29, wherein the pharmaceutical composition comprises the compound of Formula I and the compound of Formula II in a weight ratio in the range of from 1:250 to 1:550.

32. The pharmaceutical composition according to claim 29, wherein the pharmaceutical composition comprises the compound of Formula I and the compound of Formula II in a weight ratio in the range of from 1:300 to 1:500.

33. The pharmaceutical composition according to claim 29, wherein the pharmaceutical composition comprises the compound of Formula I and the compound of Formula II in a weight ratio in the range of from 1:285 to 1:400.

34. A method for treating a central nervous system disorder in a patient in need thereof, wherein the method comprises administering to the patient a therapeutically effective amount of the pharmaceutical composition according to claim 29;

wherein the central nervous system disorder is selected from the group consisting of a bipolar disorder, major depressive disorder, and schizophrenia.

35. The method according to claim 34, wherein the bipolar disorder is bipolar depression.

* * * * *

UNITED STATES PATENT AND TRADEMARK OFFICE
CERTIFICATE OF CORRECTION

PATENT NO. : 12,122,792 B2
APPLICATION NO. : 18/240951
DATED : October 22, 2024
INVENTOR(S) : Li et al.

It is certified that error appears in the above-identified patent and that said Letters Patent is hereby corrected as shown below:

In the Specification

Column 1, Line 15, "is an a continuation" should be changed to "is a continuation"

Column 2, Line 26, "scrotonin transporter" should be changed to "serotonin transporter"

Column 3, Line 52, "malcic, hydroxymalcic" should be changed to "maleic, hydroxymaleic"

Column 14, Line 46, "Phase 11 Discovery" should be changed to "Phase II Discovery"

In the Claims

Column 29, Line 2, Claim 29, "1)" should be changed to "(i)"

Signed and Sealed this
Third Day of December, 2024

Katherine Kelly Vidal
*Director of the United States Patent and Trademark Office*